(12) United States Patent
Dawson et al.

(10) Patent No.: US 9,896,663 B2
(45) Date of Patent: Feb. 20, 2018

(54) LEUKAEMIA STEM CELL LINE, ITS METHOD OF PRODUCTION AND USES THEREOF

(71) Applicant: Peter MacCallum Cancer Institute, East Melbourne, Victoria (AU)

(72) Inventors: Mark A. Dawson, Hawthorn East (AU); Chun Yew Fong, Melbourne (AU)

(73) Assignee: Peter MacCallum Cancer Institute, East Melbourne, Victoria (AU)

( * ) Notice: Subject to any disclaimer, the term of this patent is extended or adjusted under 35 U.S.C. 154(b) by 22 days.

(21) Appl. No.: 15/067,991

(22) Filed: Mar. 11, 2016

(65) Prior Publication Data
US 2017/0260510 A1   Sep. 14, 2017

(51) Int. Cl.
*C12N 5/09* (2010.01)
*G01N 33/50* (2006.01)

(52) U.S. Cl.
CPC ....... *C12N 5/0694* (2013.01); *G01N 33/5011* (2013.01); *G01N 33/5044* (2013.01); *C12N 2501/065* (2013.01)

(58) Field of Classification Search
CPC ............. C12N 5/0694; G01N 33/5011; G01N 33/5044
USPC ....................................................... 435/325
See application file for complete search history.

(56) References Cited

PUBLICATIONS

Chun Yew Fong et al., "BET inhibitor resistance emerges from leukaemia stem cells," Nature 538:525 (2015).
Sahai et al., "BET bromodomain inhibitors block growth of pancreatic cancer cells in three-dimensional collagen," Molecular Cancer Therapeutics 13(7):1907-1917 (2014).
Rathert et al.. "Transcriptional plasticity promotes primary and acquired resistance to BET inhibition," Nature 525:543-547 (2015).
Krivtsov et al., Cell of origin determines clinically relevant subtypes of MLL-rearranged AML, Leukemia, 27:852-860 (2013).
Shi & Vakoc, The mechanisms behind the therapeutic activity of BET bromodomain inhibition, Molecular Cell 54:728-736 (2014).
Owen et al., "The structural basis for the recognition of acetylated histone H4 by the bromodomain of histone acetyltransferase Gcn5p," EMBO Journal 19:6141-6149 (2000).
Dawson et al., "Recurrent mutations, including NPM1c, activate a BRD4-dependent core transcriptional program in acute myeloid leukemia," Leukemia, 28:311-320 (2014).
Dawson et al., "Inhibition of BET recruitment to chromatin as an effective treatment for MLL-fusion leukaemia," Nature, 478:529-533 (2011).
Zuber et al., "RNAi screen identifies Brd4 as a therapeutic target in acute myeloid leukaemia," Nature, 478:524-528 (2011).
Connie J. Eaves, "Henriatopoietic stem cells: concepts, definitions, and the new reality," Blood, 125(17):2605-2613 (2015).
Li & Durbin, "Fast and accurate short read alignment with Burrows-Wheeler transform," Bioinformatics, 25:1754-1760 (2009).
Koboldt et al., "VarScan 2: Somatic mutation and copy number alteration discovery in cancer by exome sequencing," 2012, Genome Research, 22:568-576.
Cibulskis et al., "Sensitive detection of somatic point mutations in impure and heterogeneous cancer samples," 2013, Nature Biotechnology, 31:213-219.
McKenna et al., "The Genome Analysis Toolkit: A MapReduce framework for analyzing next-generation DNA sequencing data," 2010, Genome Research, 20:1297-1303.
McLaren et al., "Deriving the consequences of genomic variants with the Ensembl API and SNP Effect Predictor," 2010, Bioinformatics, 26:2069-2070.
Karolchik et al., "The UCSC Table Browser data retrieval tool," 2004, Nucleic Acids Research, 32: D493-496.
Zhang et al., "Model-based Analysis of ChIP-Seq (MACS)," 2008, Genome Biology, 9:R137.
Liao et al., "The Subread aligner: fast, accurate and scalable read mapping by seed-and-vote," 2013, Nucleic Acids Research, 41:e108.
Wu et al., "ROAST: rotation gene set tests for complex microarray experiments," 2010, Bioinformatics, 26:2176-2182.
Aravind Subramanian et al., "Gene set enrichment analysis: A knowledge-based approach for interpreting genome-wide expression profiles," 2005, PNAS, 102:15545-15550.
Mouse Genome Informatics, http://www.informatics.jax.org, downloaded Apr. 14, 2017.
Matthew E. Ritchie et al., "limma powers differential expression analyses for RNA-sequencing and microarray studies," 2015, Nucleic Acids Research 43(7):e47.
Wang et al., "The Wnt/β-catenin Pathway is Required for the Development of Leukemia Stem Cells in AML," 2010, Science, 327:1650-1653.

*Primary Examiner* — Yan Xiao
(74) *Attorney, Agent, or Firm* — Fish & Richardson P.C.

(57) ABSTRACT

Bromodomain and extra terminal protein (BET) resistant leukemic cell lines and methods for producing such cell lines are described as are methods for using such cell lines in screening assays to identify therapeutic agents. The cell lines can be generated from haematopoietic stem and progenitor cells (HSPCs) that are clonally enriched by serially exposing c-kit positive cells to a BET inhibitor.

10 Claims, 19 Drawing Sheets

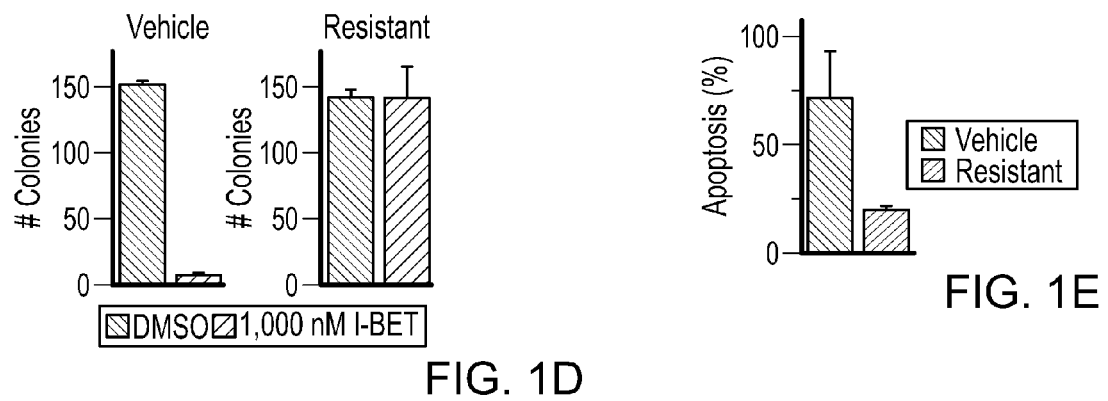
FIG. 1D
FIG. 1E
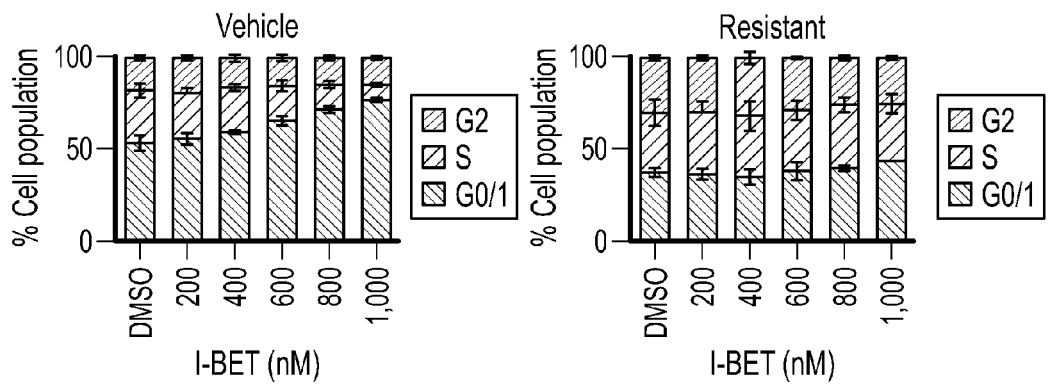
FIG. 1F

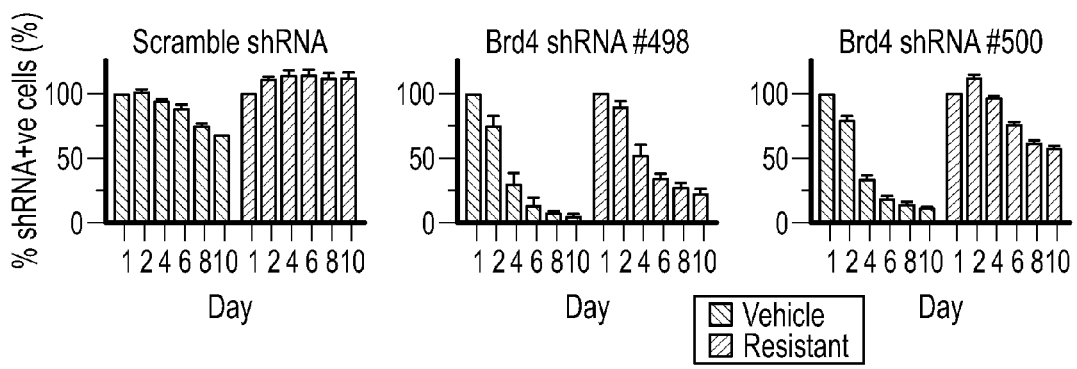
FIG. 1G
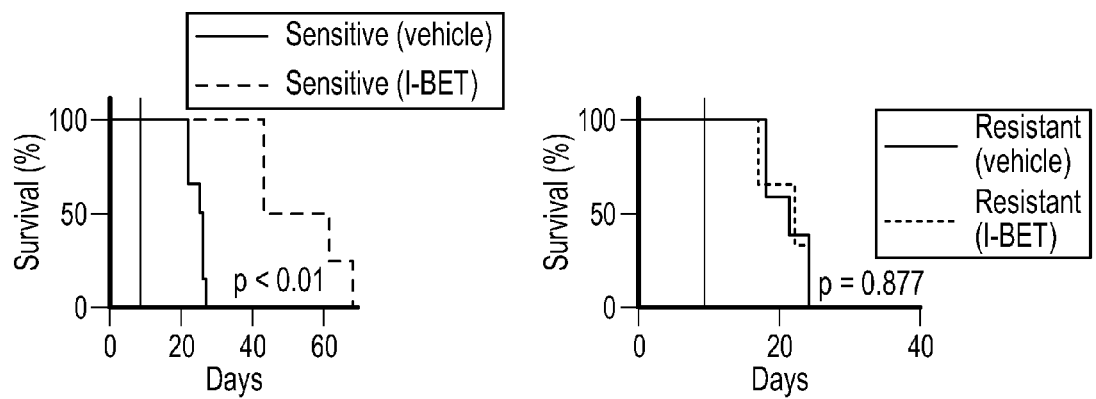
FIG. 1H
FIG. 1I

SEQUENCE LISTING

```
<160> NUMBER OF SEQ ID NOS: 48

<210> SEQ ID NO 1
<211> LENGTH: 19
<212> TYPE: DNA
<213> ORGANISM: Artificial
<220> FEATURE:
<223> OTHER INFORMATION: Primer

<400> SEQUENCE: 1
cggattatca caaaattat                                                  19

<210> SEQ ID NO 2
<211> LENGTH: 19
<212> TYPE: DNA
<213> ORGANISM: Artificial
<220> FEATURE:
<223> OTHER INFORMATION: Primer
```

```
<400> SEQUENCE: 2
actatgttta caaattgtt                                               19

<210> SEQ ID NO 3
<211> LENGTH: 19
<212> TYPE: DNA
<213> ORGANISM: Artificial
<220> FEATURE:
<223> OTHER INFORMATION: Primer

<400> SEQUENCE: 3
aggacttcaa cactatgtt                                               19

<210> SEQ ID NO 4
<211> LENGTH: 19
<212> TYPE: DNA
<213> ORGANISM: Artificial
<220> FEATURE:
<223> OTHER INFORMATION: Primer

<400> SEQUENCE: 4
agcagaacaa accaaagaa                                               19

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
ggagtggcag aaagcaacac                                              20

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
aaacactggc tgtttcgtga                                              20

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
gagcccaaga ccgtctactg                                              20

<210> SEQ ID NO 8
<211> LENGTH: 21
<212> TYPE: DNA
<213> ORGANISM: Artificial
<220> FEATURE:
<223> OTHER INFORMATION: Primer

<400> SEQUENCE: 8
gctatttctt tctgcgtgca t                                            21

<210> SEQ ID NO 9
<211> LENGTH: 20
```

```
<212> TYPE: DNA
<213> ORGANISM: Artificial
<220> FEATURE:
<223> OTHER INFORMATION: Primer

<400> SEQUENCE: 9
tgggctgcct cagaatgtat                                                     20

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
ccagtgtctg tgccattagg                                                     20

<210> SEQ ID NO 11
<211> LENGTH: 20
<212> TYPE: DNA
<213> ORGANISM: Artificial
<220> FEATURE:
<223> OTHER INFORMATION: Primer

<400> SEQUENCE: 11
gccagtgagt gtatgcagga                                                     20

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12
gcctgggcca ttagcactat                                                     20

<210> SEQ ID NO 13
<211> LENGTH: 20
<212> TYPE: DNA
<213> ORGANISM: Artificial
<220> FEATURE:
<223> OTHER INFORMATION: Primer

<400> SEQUENCE: 13
tctgcacgac tactgtgaca                                                     20

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
ggcatctctg tactctcggg                                                     20

<210> SEQ ID NO 15
<211> LENGTH: 18
<212> TYPE: DNA
<213> ORGANISM: Artificial
<220> FEATURE:
<223> OTHER INFORMATION: Primer

<400> SEQUENCE: 15
```
caagccacca ccccctaca                                                    18

<210> SEQ ID NO 16
<211> LENGTH: 15
<212> TYPE: DNA
<213> ORGANISM: Artificial
<220> FEATURE:
<223> OTHER INFORMATION: Primer

<400> SEQUENCE: 16
ttgccgcccg aatgg                                                        15

<210> SEQ ID NO 17
<211> LENGTH: 20
<212> TYPE: DNA
<213> ORGANISM: Artificial
<220> FEATURE:
<223> OTHER INFORMATION: Primer

<400> SEQUENCE: 17
ctgcatgagg cacgctatgt                                                   20

<210> SEQ ID NO 18
<211> LENGTH: 20
<212> TYPE: DNA
<213> ORGANISM: Artificial
<220> FEATURE:
<223> OTHER INFORMATION: Primer

<400> SEQUENCE: 18
aggaaaatgg ctgtggtcag                                                   20

<210> SEQ ID NO 19
<211> LENGTH: 20
<212> TYPE: DNA
<213> ORGANISM: Artificial
<220> FEATURE:
<223> OTHER INFORMATION: Primer

<400> SEQUENCE: 19
atcacacgca ccagctcttc                                                   20

<210> SEQ ID NO 20
<211> LENGTH: 20
<212> TYPE: DNA
<213> ORGANISM: Artificial
<220> FEATURE:
<223> OTHER INFORMATION: Primer

<400> SEQUENCE: 20
ggacaatggc actcatgtca                                                   20

<210> SEQ ID NO 21
<211> LENGTH: 20
<212> TYPE: DNA
<213> ORGANISM: Artificial
<220> FEATURE:
<223> OTHER INFORMATION: Primer

<400> SEQUENCE: 21
ggctacaacc tgacgcacat                                                   20

<210> SEQ ID NO 22
<211> LENGTH: 20
<212> TYPE: DNA
<213> ORGANISM: Artificial

```
<220> FEATURE:
<223> OTHER INFORMATION: Primer

<400> SEQUENCE: 22
cagaattggt gcacctccag                                                    20

<210> SEQ ID NO 23
<211> LENGTH: 20
<212> TYPE: DNA
<213> ORGANISM: Artificial
<220> FEATURE:
<223> OTHER INFORMATION: Primer

<400> SEQUENCE: 23
ggtgctgagt atgtcgtgga                                                    20

<210> SEQ ID NO 24
<211> LENGTH: 20
<212> TYPE: DNA
<213> ORGANISM: Artificial
<220> FEATURE:
<223> OTHER INFORMATION: Primer

<400> SEQUENCE: 24
cggagatgat gaccctttg                                                     20

<210> SEQ ID NO 25
<211> LENGTH: 20
<212> TYPE: DNA
<213> ORGANISM: Artificial
<220> FEATURE:
<223> OTHER INFORMATION: Primer

<400> SEQUENCE: 25
ttggagccac tgattacacg                                                    20

<210> SEQ ID NO 26
<211> LENGTH: 20
<212> TYPE: DNA
<213> ORGANISM: Artificial
<220> FEATURE:
<223> OTHER INFORMATION: Primer

<400> SEQUENCE: 26
ccaactgatc cacaccactg                                                    20

<210> SEQ ID NO 27
<211> LENGTH: 19
<212> TYPE: DNA
<213> ORGANISM: Artificial
<220> FEATURE:
<223> OTHER INFORMATION: Primer

<400> SEQUENCE: 27
tgagccccta gtgctgcat                                                     19

<210> SEQ ID NO 28
<211> LENGTH: 19
<212> TYPE: DNA
<213> ORGANISM: Artificial
<220> FEATURE:
<223> OTHER INFORMATION: Primer

<400> SEQUENCE: 28
agcccgactc cgacctctt                                                     19
```

<210> SEQ ID NO 29
<211> LENGTH: 20
<212> TYPE: DNA
<213> ORGANISM: Artificial
<220> FEATURE:
<223> OTHER INFORMATION: Primer

<400> SEQUENCE: 29
cggacagcag tgtagatgga					20

<210> SEQ ID NO 30
<211> LENGTH: 20
<212> TYPE: DNA
<213> ORGANISM: Artificial
<220> FEATURE:
<223> OTHER INFORMATION: Primer

<400> SEQUENCE: 30
cttcacactg cgatgcattt					20

<210> SEQ ID NO 31
<211> LENGTH: 20
<212> TYPE: DNA
<213> ORGANISM: Artificial
<220> FEATURE:
<223> OTHER INFORMATION: Primer

<400> SEQUENCE: 31
gctgtgcatc tacaccgaca					20

<210> SEQ ID NO 32
<211> LENGTH: 20
<212> TYPE: DNA
<213> ORGANISM: Artificial
<220> FEATURE:
<223> OTHER INFORMATION: Primer

<400> SEQUENCE: 32
ccacttgagc ttgttcacca					20

<210> SEQ ID NO 33
<211> LENGTH: 20
<212> TYPE: DNA
<213> ORGANISM: Artificial
<220> FEATURE:
<223> OTHER INFORMATION: Primer

<400> SEQUENCE: 33
gaccacaagc agagtgctga					20

<210> SEQ ID NO 34
<211> LENGTH: 20
<212> TYPE: DNA
<213> ORGANISM: Artificial
<220> FEATURE:
<223> OTHER INFORMATION: Primer

<400> SEQUENCE: 34
cttgcattcc accagcttct					20

<210> SEQ ID NO 35
<211> LENGTH: 20
<212> TYPE: DNA
<213> ORGANISM: Artificial
<220> FEATURE:
<223> OTHER INFORMATION: Primer

```
<400> SEQUENCE: 35
ttcctgtcag cctgctacct                                                20

<210> SEQ ID NO 36
<211> LENGTH: 20
<212> TYPE: DNA
<213> ORGANISM: Artificial
<220> FEATURE:
<223> OTHER INFORMATION: Primer

<400> SEQUENCE: 36
cgtagtggat gtggttgtgc                                                20

<210> SEQ ID NO 37
<211> LENGTH: 19
<212> TYPE: DNA
<213> ORGANISM: Artificial
<220> FEATURE:
<223> OTHER INFORMATION: Primer

<400> SEQUENCE: 37
ctggtgctcc atgaggaga                                                 19

<210> SEQ ID NO 38
<211> LENGTH: 20
<212> TYPE: DNA
<213> ORGANISM: Artificial
<220> FEATURE:
<223> OTHER INFORMATION: Primer

<400> SEQUENCE: 38
cctgcctctt ttccacagaa                                                20

<210> SEQ ID NO 39
<211> LENGTH: 20
<212> TYPE: DNA
<213> ORGANISM: Artificial
<220> FEATURE:
<223> OTHER INFORMATION: Primer

<400> SEQUENCE: 39
atggcaaata gaggaagcgg                                                20

<210> SEQ ID NO 40
<211> LENGTH: 21
<212> TYPE: DNA
<213> ORGANISM: Artificial
<220> FEATURE:
<223> OTHER INFORMATION: Primer

<400> SEQUENCE: 40
tggagaatag atcgaagcaa g                                              21

<210> SEQ ID NO 41
<211> LENGTH: 19
<212> TYPE: DNA
<213> ORGANISM: Artificial
<220> FEATURE:
<223> OTHER INFORMATION: Primer

<400> SEQUENCE: 41
ttcaacaccc cagccatgt                                                 19

<210> SEQ ID NO 42
```

```
<211> LENGTH: 18
<212> TYPE: DNA
<213> ORGANISM: Artificial
<220> FEATURE:
<223> OTHER INFORMATION: Primer

<400> SEQUENCE: 42
gccagtggta cggccaga                                                 18

<210> SEQ ID NO 43
<211> LENGTH: 20
<212> TYPE: DNA
<213> ORGANISM: Artificial
<220> FEATURE:
<223> OTHER INFORMATION: Primer

<400> SEQUENCE: 43
acgggaagct tgtcatcaat                                               20

<210> SEQ ID NO 44
<211> LENGTH: 20
<212> TYPE: DNA
<213> ORGANISM: Artificial
<220> FEATURE:
<223> OTHER INFORMATION: Primer

<400> SEQUENCE: 44
tggactccac gacgtactca                                               20

<210> SEQ ID NO 45
<211> LENGTH: 20
<212> TYPE: DNA
<213> ORGANISM: Artificial
<220> FEATURE:
<223> OTHER INFORMATION: Primer

<400> SEQUENCE: 45
gtcaccttta ccccgactca                                               20

<210> SEQ ID NO 46
<211> LENGTH: 20
<212> TYPE: DNA
<213> ORGANISM: Artificial
<220> FEATURE:
<223> OTHER INFORMATION: Primer

<400> SEQUENCE: 46
tccaggcaca tctcagtttg                                               20

<210> SEQ ID NO 47
<211> LENGTH: 20
<212> TYPE: DNA
<213> ORGANISM: Artificial
<220> FEATURE:
<223> OTHER INFORMATION: Primer

<400> SEQUENCE: 47
tctttgatgg gctcaatggt                                               20

<210> SEQ ID NO 48
<211> LENGTH: 20
<212> TYPE: DNA
<213> ORGANISM: Artificial
```

```
<220> FEATURE:
<223> OTHER INFORMATION: Primer

<400> SEQUENCE: 48
ttcccttcac ctgatgaacc                                                    20
```

LEUKAEMIA STEM CELL LINE, ITS METHOD OF PRODUCTION AND USES THEREOF

FIELD OF INVENTION

The present invention relates to a leukaemia stem cell line, its method of production and use for the identification of drug candidates having pharmacological properties.

DESCRIPTION OF THE RELATED ART

Bromodomain and extra terminal protein (BET) inhibitors are a new class of targeted therapeutics that interact directly with the bromodomains of BET family proteins to competitively inhibit binding of acetylated chromatin (Dawson et al 2012 *New England Journal of Medicine* 367: 647-657). These targeted therapeutics have demonstrated efficacy for the treatment of haematopoietic tumours, including acute myeloid leukaemia (AML) (Herait et al 2014 *Cancer Research* 74: CT231); and solid tumours, including pancreatic ductal adenocarcinoma (PDAC) (Sahai et al 2014 *Molecular Cancer Therapeutics* 13(7): 1907-1917). In order to maximise the clinical efficacy of these inhibitors, it is crucial to understand potential mechanisms of drug resistance to determine how best to combine BET inhibitors with other therapies.

Mechanisms by which drug resistance occurs include increased rates of drug efflux, alterations in drug metabolism, mutation of drug targets, activation of survival signalling pathways, inactivation of death pathways, epigenetic changes, tumour micro environmental changes and treatment-induced selection of resistant cells from heterogeneous tumour populations (including cancer stem cells). Such mechanisms are generally investigated by the generation of isogenic resistant and sensitive cell lines, which allow for the direct comparison of cellular phenotype prior to and after the development of resistance. Accordingly, a parental cell line that is sensitive to the drug of interest is exposed to incrementally increased concentrations of the drug until subpopulations of resistant cells emerge. These resistant cells are then compared with the parental cell line to identify genetic, molecular or biochemical differences that may be attributed to the resistant phenotype. However, previous studies that have attempted to investigate BET inhibitor resistance mechanisms in AML have failed to enrich for populations of haematopoietic stem and progenitor cells (Rathert et al 2015 *Nature* 525: 543-547) and the molecular and cellular mechanisms that govern sensitivity and resistance to BET inhibitors in AML remain largely unknown.

The present invention is concerned with the development of a novel cell line model of leukaemia that is isolated and grown using a BET inhibitor.

SUMMARY OF INVENTION

In a first aspect, the present invention provides a method for preparing a leukaemia stem cell line, the method comprising isolating c-kit positive cells from the whole bone marrow of a mammal; immortalising the isolated cells; serially re-plating the immortalised cells in cytokine-supplemented methylcellulose containing BET inhibitor; selecting individual BET inhibitor resistant colonies and transferring to liquid culture containing a BET inhibitor; and incrementally increasing the concentration of BET inhibitor in the liquid culture to greater than the IC70 value of the parental cell line, wherein the surviving cells are isolated leukaemia stem cells.

In a second aspect, the present invention provides a mammalian leukaemia stem cell line prepared according to the present invention.

In a third aspect, the present invention provides a murine leukaemia stem cell line, wherein the cell line is deposited at CellBank Australia under the accession number CBA20150028 on 19 Nov. 2015.

In a forth aspect, the present invention provides a use of a mammalian leukaemia stem cell line prepared according to the present invention in a screening method to identify an agent with a pharmacological property, said method comprising exposing cells to an agent or agents; analysing the cells following exposure to an agent or agents; and identifying at least one agent having the pharmacological property.

In a fifth aspect, the present invention provides a use of a murine leukaemia stem cell line deposited at CellBank Australia under the accession number CBA20150028 on 19 Nov. 2015 in a screening method to identify an agent with a pharmacological property, said method comprising exposing cells to an agent or agents; analysing the cells following exposure to an agent or agents; and identifying at least one agent having the pharmacological property.

In a sixth aspect, the present invention provides an agent identified by the use of a screening method according to the present invention.

BRIEF DESCRIPTION OF THE FIGURES

FIG. 1A-FIG. 1I shows the method for establishing a murine leukaemia stem cell line. (A) A schematic representation of the strategy for the generation of resistant clones (HSPC, haematopoietic stem and progenitor cells). (B) A graphical representation of time (day; x-axis) against cell number (cells mL$^{-1}$; y-axis) where cells have been treated with 1 μM I-BET showing that resistant clones stably grow at various concentrations including those greater than the IC$_{90}$ value of the parental and vehicle-treated cells. (C) A graphical representation of time (day; x-axis) against cell number (cells mL$^{-1}$; y-axis) where cells have been treated with 100 nM JQ1 showing that resistant clones exhibit cross-resistance to chemically distinct BET inhibitor, JQ1. (D) A graphical representation of 1,000 nM I-BET or DMSO-treated cells (x-axis) against number of colonies formed (y-axis) showing that the parental cell line (vehicle) remains sensitive to I-BET-mediated suppression of clonogenic capacity. (E) A graphical representation of resistant or parental (vehicle) cells (x-axis) against percentage of apoptotic cells (%; y-axis) showing that parental cells remain sensitive to I-BET-mediated induction of apoptosis. (F) A graphical representation of concentration of I-BET (nM; x-axis) against cell population (%; y-axis) in resistant or parental (vehicle) cells showing that parental cells remain sensitive to I-BET-mediated induction of cell cycle arrest. (G) A graphical representation of time (day; x-axis) against shRNA-positive cells (%; y-axis) showing that resistant cells are significantly less susceptible to genetic depletion of BRD4. (H) A graphical representation of time (days; x-axis) against survival (%; y-axis) showing that treatment with I-BET leads to a significant survival advantage in recipients of the parental cell line (P<0.01; n=6, log-rank test). (I) A graphical representation of time (days; x-axis) against survival (%; y-axis) showing that the survival advantage associated with I-BET treatment is abrogated in recipients of the resistant cell line (P=0.877; n=6, log-rank test).

DETAILED DESCRIPTION OF THE INVENTION

Figure 1A:
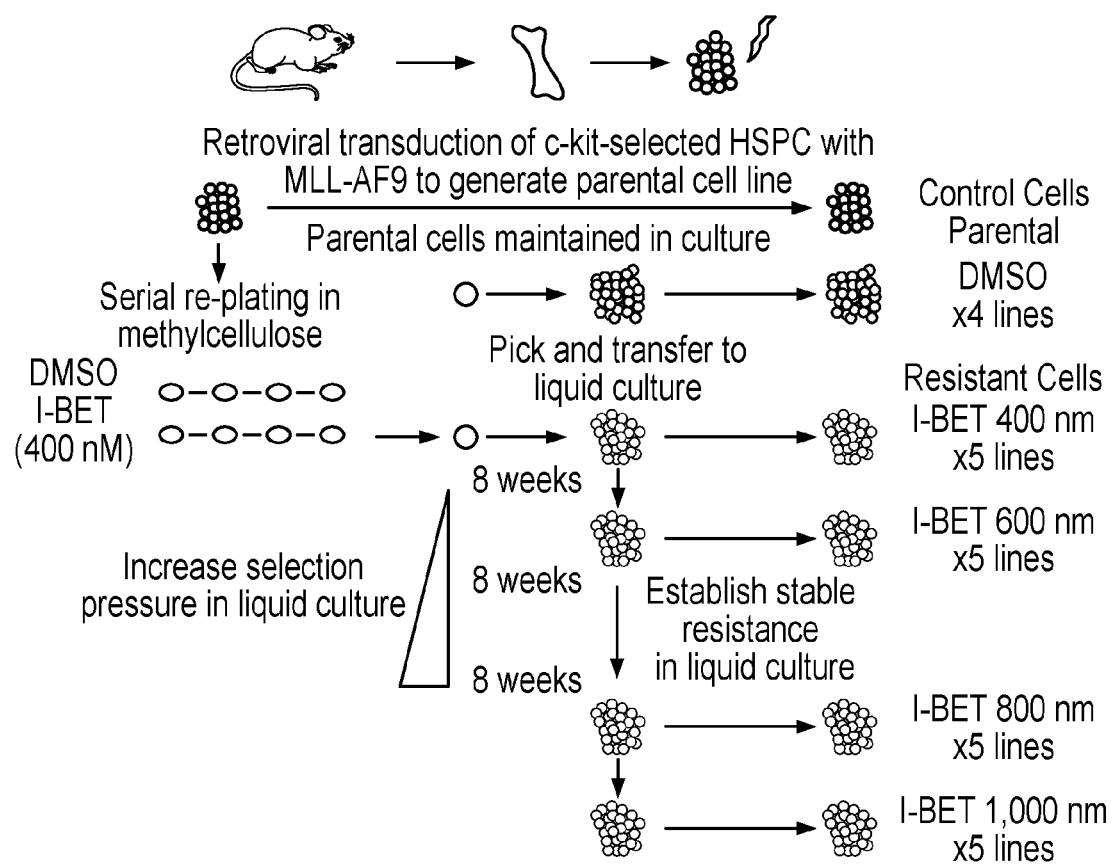
Figure 1B:
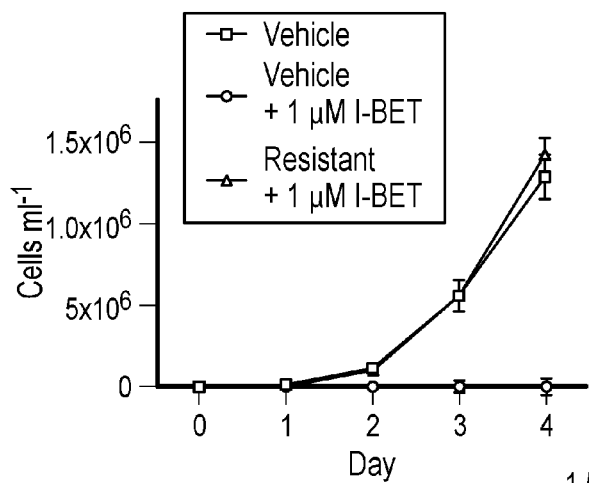

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The reference in this specification to any prior publication (or information derived from it), or to any matter which is known, is not, and should not be taken as an acknowledgement or admission or any form of suggestion that prior publication (or information derived from it) or known matter forms part of the common general knowledge in the field of endeavour to which this specification relates.

All publications mentioned in this specification are herein incorporated by reference in their entirety.

It must be noted that, as used in this specification, the singular forms "a" and "the" include plural aspects unless the context clearly dictates otherwise. Thus, for example, reference to "an agent" includes a single agent, as well as two or more agents; reference to "a property" includes a single property, as well as two or more properties; and so forth.

The BET family of adaptor proteins (BRD2/BRD3/BRD4 and BRDT) regulate transcription by binding acetylated chromatin at discrete locations across the chromosome, where they recruit other regulatory molecules, such as RNA polymerase II, to influence gene expression, DNA repair, replication and chromosome condensation (Shi & Vakoc 2014 *Molecular Cell* 54: 728-736). BET proteins have a common structural design, featuring two tandem bromodomains at the N-terminal end of the protein, which recognise acetylated lysine residues on histone tails and other nuclear proteins (Shi & Vakoc 2014 supra). The bromodomains share a conserved fold with four α helices ($α_Z$, $α_A$, $α_B$ and $α_C$) linked by diverse loop regions. Binding of acetylated chromatin to the bromodomains is mediated by a central hydrophobic cavity, which forms a hydrogen bond between acetyl-lysine and an asparagine residue present within the bromodomain (Owen et al 2000 *EMBO Journal* 19: 6141).

Inhibition of BET proteins using small molecules has been demonstrated to directly silence MYC oncogene expression by disrupting BET protein binding at the MYC locus. Given that MYC is a critical regulator of cell proliferation and survival during the tumorigenesis of the majority of human tumours, BET inhibitors provide a novel mechanism to target MYC-driven tumours. BET inhibitors have proven to be particularly effective for the treatment of haematological malignancies, where potent anti-proliferative effects associated with cell cycle arrest and cellular senescence have been reported (Dawson et al. 2014, *Leukemia*, 28: 311-320; Dawson et al. 2011, *Nature*, 478: 529-533; Zuber et al. 2011, *Nature*, 478: 524-528). Consequently, the development of appropriate experimental models to evaluate resistance mechanisms is crucial to optimise the clinical efficacy of these drugs.

The present invention is predicated, in part, on the finding that, a stable leukaemia stem cell line may be generated where haematopoietic stem and progenitor cells (HSPCs) are clonally enriched for by serially exposing c-kit positive cells to $IC_{40}$ concentrations of a BET inhibitor in methylcellulose-based media, followed by the culturing of selected cells in incrementally increasing concentrations of BET inhibitor until cells are resistant to at least the $IC_{70}$ concentration of the BET inhibitor. The inventors of the presently claimed invention have surprisingly shown that BET inhibitor resistance arises from the leukemic stem cell compartment allowing for the selective isolation of leukaemia stem cells using this in vitro culture method.

Accordingly, in a first aspect, the present invention provides a method for preparing a mammalian leukaemia stem cell cell line, the method comprising isolating c-kit positive cells from whole bone marrow of a mammal; immortalising the isolated cells; serially re-plating the immortalised cells in cytokine-supplemented methylcellulose containing BET inhibitor; selecting individual BET inhibitor resistant colonies and transferring to liquid culture, wherein the liquid culture contains a BET inhibitor; and incrementally increasing the concentration of BET inhibitor in the liquid culture to greater than the $IC_{70}$ value of the parental cell line, wherein the surviving cells are selected as BET inhibitor resistant leukaemia stem cells.

As used herein the term "preparing" means generating a leukaemia stem cell line.

As used herein the term "bromodomain and extra terminal protein inhibitor" or "BET inhibitor" refer to a class of targeted therapeutic that is used to prevent binding of the bromodomains of BET family proteins to acetylated chromatin. Examples of inhibitors encompassed within the term "BET inhibitor" include small molecule inhibitors I-BET 151, I-BET 762, JQ1, OTX-015, TEN-010, CPI-203, CPI-0610, RVX-208, PFI-1 and LY294002.

In an embodiment, the BET inhibitor of the present invention is I-BET 151 or JQ1.

In another embodiment, the BET inhibitor of the present invention is I-BET 151.

The term "inhibiting" and variations thereof, such as "inhibition" and "inhibits", as used herein, do not necessarily imply the complete inhibition of the specified event, activity or function. Rather, the inhibition may be to an extent, and/or for a time, sufficient to produce the desired effect. Inhibition may be prevention, retardation, reduction, abrogation or otherwise hindrance of an event activity or function. Such inhibition may be in magnitude and/or be temporal in nature. In particular contexts, the terms "inhibit" and "prevent", and variations thereof may be used interchangeably.

Drug resistance limits the effectiveness of drugs used to treat diseases. In the context of cancer, tumour cells may be intrinsically resistant. Alternatively, drug resistance may also be acquired during treatment of tumours that are initially sensitive to therapy. Tumour cells can acquire resistance by a range of mechanisms, including increased rates of drug efflux, alterations in drug metabolism, mutation of drug targets, activation of survival signalling pathways, inactivation of death pathways, epigenetic changes, tumour micro environmental changes and treatment-induced selection of resistant cells from heterogeneous tumour populations (including cancer stem cells).

The term "resistant" and variations thereof, as used herein does not necessarily imply the complete resistance to the specified drug. Rather the resistance may be to an extent and/or for a time. Resistance may be immunity, tolerance, or otherwise hindrance of the efficacy of drug activity or function.

Cells of the present invention will be resistant to a concentration of BET inhibitor at greater than the $IC_{70}$ value of the parental cell line. Reference to "greater than the $IC_{70}$ value of the parental cell line" means greater than the $IC_{70}$, $IC_{71}$, $IC_{72}$, $IC_{73}$, $IC_{74}$, $IC_{75}$, $IC_{76}$, $IC_{77}$, $IC_{78}$, $IC_{79}$, $IC_{80}$, $IC_{81}$, $IC_{82}$, $IC_{83}$, $IC_{84}$, $IC_{85}$, $IC_{86}$, $IC_{87}$, $IC_{88}$, $IC_{89}$, $IC_{90}$, $IC_{91}$, $IC_{92}$, $IC_{93}$, $IC_{94}$, $IC_{95}$, $IC_{96}$, $IC_{97}$, $IC_{98}$ or $IC_{99}$ value of the parental cell line.

In an embodiment, the mammalian leukaemia stem cell line will be resistant to a concentration of BET inhibitor at greater than the $IC_{70}$ value of the parental cell line.

In another embodiment, the mammalian leukaemia stem cell line will be resistant to a concentration of BET inhibitor at greater than the $IC_{80}$ value of the parental cell line.

In yet another embodiment, the mammalian leukaemia stem cell line will be resistant to a concentration of BET inhibitor at greater than the $IC_{90}$ value of the parental cell line.

As used herein, the term "IC value" means the maximal inhibitory concentration to inhibit the parental cell line to a given percentage. For example, the $IC_{70}$ value of the parental cell line means the concentration of a drug that is required for 70% inhibition of the parental cell line. Alternatively, the IC$_{80}$ value of the parental cell line means the concentration of a drug that is required for 80% inhibition of the parental cell line.

The leukaemia stem cells of the presently claimed invention may be human or mammalian, wherein the mammal is of economical importance and/or social importance to humans, for instance, carnivores other than humans (e.g., cats and dogs), swine (e.g., pigs, hogs and wild boars), ruminants (e.g., cattle, oxen, sheep, giraffes, deer, goats, bison and camels), horses and birds including those kinds of birds that are endangered, kept in zoos, and fowls, and more particularly domesticated fowl, e.g., poultry, such as turkeys, chickens, ducks, geese, guinea fowl, and the like, as they are also of economical importance to humans. The term "mammalian" does not denote a particular age. Thus, both adult and newborn mammals are intended to be covered.

In an embodiment, the mammal is a mouse.

In another embodiment, the mouse is a C57BL/6 mouse.

As used herein, the term "leukaemia stem cells" means a heterogeneous population of malignant hematopoietic stem and progenitor cells derived from whole bone marrow.

As used herein, the terms "hematopoietic stem and progenitor cells" or "HSPCs" mean a heterogeneous population of stem cells derived from whole bone marrow.

"Hematopoietic stem cells" or "HSCs" are undifferentiated, multi-potent stem cells capable of self-renewal and the generation all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art.

As used herein, the term "potency" refers to the sum of all developmental options accessible to the cell. A person skilled in the art would recognize that cell potency is a continuum, ranging from the most plastic cell, a totipotent stem cell, which has the most developmental potency to the least plastic cell, a terminally differentiated cell, which has the least developmental potency. The continuum of cell potency includes, but is not limited to totipotent cells, pluripotent cells, multipotent cells, oligo potent cells, unipotent cells and terminally differentiated cells. Multipotent stem cells are lineage restricted stem cells (e.g. hematopoietic stem cells), which are capable of forming multiple cell types of one lineage.

As used herein, the term "self-renewal" refers to the process by which a stem cell divides to generate one (asymmetric division) or two (symmetric division) daughter cells with development potentials that are indistinguishable from those of the mother cell. Self-renewal involves both proliferation and the maintenance of an undifferentiated state.

"Hematopoietic progenitor cells" or "HPCs" are immature HSCs that are precursors to a fully differentiated hematopoietic cell. HPCs are capable of proliferating, but they have a limited capacity to differentiate into more that one type of cell type, for example, lymphoid progenitor cells can differentiate into natural killer cells, T lymphocytes and B lymphocytes; while myeloid progenitor cells can differentiate into neutrophils, basophils, eosinophils, monocytes, macrophages, platelets, erythrocytes and dendritic cells.

HSPCs may be identified according to certain phenotypic or genotypic markers. For example, HSPCs may be identified by their small size, lack of lineage (lin) markers, low staining (side population) with vital dyes such as rhodamine 123 (rhodamine$^{DULL}$, also called rho$^{lo}$) or Hoechst 33342, and presence of various antigenic markers on their surface, many of which belong to the cluster of differentiation series (e.g., CD34, CD38, CD90, CD133, CD105, CD45, and c-kit, the receptor for stem cell factor). HSPCs are mainly negative for the markers that are typically used to detect lineage commitment, and, thus, are often referred to as Lin (−) cells.

It should be understood that the presently claimed invention is not limited to malignant cell lines, their method of production and uses thereof. According to another aspect of the present invention the methods described herein may also be used to isolate normal haematopoietic stem and progenitor cells.

The term "isolated" as used herein means material that is removed from its original environment. For example, a cell is isolated if it is separated from some or all of the components that normally accompany it in its native state. For example, an "isolated population of cells," an "isolated source of cells," or "isolated leukaemia stem cells" and the like, as used herein, refer to in vitro or ex vivo separation of one or more cells from their natural cellular environment, and from association with other components of the tissue or organ, i.e., it is not significantly associated with in vivo substances.

According to the method of the present invention, leukaemia stem cells are isolated from whole bone marrow by initially isolating all HSPCs using the c-kit antigenic marker. C-kit is a tyrosine kinase growth factor receptor that is constitutively expressed by HSPCs. A c-kit positive cell may be isolated by any suitable means known in the art. For example, a c-kit positive cell may be isolated using magnetic beads conjugated to c-kit antibody, allowing for isolation of c-kit positive cells using high gradient magnetic selection. Alternatively, a c-kit positive cell may be isolated using flow cytometry, such as fluorescence activated cell sorting using a fluoro chrome conjugated c-kit antibody. Therefore, binding molecules (e.g. antibodies) reactive with c-kit or portions thereof can be used to isolate c-kit positive cells. Such binding molecules would be known to the person skilled in the art. For example, the binding molecules may be antibodies that specifically bind with c-kit or a portion thereof. Such antibodies can be polyclonal or monoclonal, and the term "antibody" encompasses full-length polyclonal or monoclonal antibodies and functional fragments thereof.

In an embodiment, HSPCs are isolated from whole bone marrow using magnetic beads.

In an embodiment, HSPCs are isolated from whole bone marrow using flow cytometry.

In order for isolated HSPCs to proliferate indefinitely in culture, the cells are immortalized using methods that are well-known in the art. For example, cells may be immortalized by transforming a construct into the cell, which contains a gene that confers the ability to grow and proliferate in culture. Such immortalizing genes include nuclear oncogenes such as v-Myc, N-Myc, T antigen and Ewing's sarcoma oncogene; cytoplasmic oncogenes such as ras and B-raf; membrane oncogenes such as neu and ret; tumor suppressor genes such as mutant p53 and mutant Rb, and other immortalizing genes such as Notch dominant negative.

In an embodiment, HSPCs are immortalized by retroviral transduction of a construct containing a gene encoding a Mixed Lineage Leukemia (MLL) fusion protein.

In an embodiment, HSPCs are immortalized with a MSCV-MLL-AF9-IRES-YFP construct. In another embodiment, HSPCs are immortalized with a MSCV-MLL-ENL construct.

This strategy selects a heterogeneous population of HSPCs that includes lineage-primed multipotent progenitors in addition to short-term and long-term HSCs. To obtain a stable leukaemia stem cell line, the inventors of the present specification have surprisingly found that an additional selection strategy that exposes HSPC single cell clones to $IC_{40}$ concentrations of a BET inhibitor generates clonally resistant HSPCs may be used to preselect resistant clones that may subsequently be exposed to higher concentrations of BET inhibitor to generate a BET inhibitor resistant cell line. Importantly, the inventors have demonstrated that BET inhibitor resistance arises from the leukemic stem cell compartment, resulting in the selective isolation of leukaemia stem cells using this in vitro culture method.

Therefore, in accordance with the present invention, immortalised c-kit positive HSPCs derived from whole bone marrow are subjected to a single cell cloning method based on the colony-forming unit (CFU) assay. The CFU assay is an in vitro functional assay for enumerating multi-potent and lineage-committed haematopoietic stem and progenitor cells (Eaves 2015 Blood 125(17): 2605-2613). Using this method, individual HSPCs proliferate and produce colonies of cells comprising different stages of maturation. Importantly, each colony is derived from a single progenitor cell or CFU.

The in vitro expansion and selection of cell according to this method requires the use of culture medium that stimulates the growth and differentiation of HSPCs and the use of a viscous or semi-solid medium to spatially restrict the progeny of single progenitor cells into a colony that can be identified and selected.

In an embodiment, methylcellulose-based medium is used to perform haematopoietic single cell cloning. The methylcellulose of the present invention may be any methylcellulose-containing media known to persons skilled in the art. Examples include methylcellulose base media, MethoCult™ and ColonyGEL™.

The methylcellulose of the present invention further comprises cytokine supplementation. Persons skilled in the art would understand that the type of cytokine(s) will depend on the cells to be prepared. For example, where the cells are human cells, examples of cytokines include recombinant human G-CSF, GM-CSF, IL-3, IL-6 and erythropoietin. Conversely, where the cells are mouse cells, examples of cytokines include recombinant mouse IL-3 and IL-6.

In an embodiment, the clonally resistant cell line of the present invention is resistant to the $IC_{40}$ concentration of a BET inhibitor.

Methods for the selection of drug resistant cell lines are well known in the art and generally involve culturing and subculturing cells in the presence of increasing concentrations of a drug. Surviving colonies of cells are further expanded in the present of higher concentrations of drug which eventually results in individual resistant cell lines and sublines of cells. As used herein, "resistance" of a cell to a drug refers to the ability of the cell to tolerate higher concentrations of a drug than a sensitive cell. Therefore, BET resistance in a cell is determined relative to appropriate BET inhibitor sensitive cells. For example, the BET inhibitor resistance of a cell that has been continually exposed to a BET inhibitor can be determined relative to the parental sensitive cell from which the drug resistant cell was derived.

The leukaemia stem cells disclosed herein were obtained by culturing and subculturing clonally resistant HSPCs in the presence of increasing concentrations of a BET inhibitor.

In an embodiment, the leukaemia stem cells of the present invention are resistant to greater than the $IC_{70}$ concentration of a BET inhibitor.

In another embodiment, the leukaemia stem cells of the present invention are resistant to greater than the $IC_{80}$ concentration of a BET inhibitor.

In yet another embodiment, the leukaemia stem cells of the present invention are resistant to greater than the $IC_{90}$ concentration of a BET inhibitor.

In terms of in vitro culture technology, the leukaemia stem cells of the present invention can be produced on either a small scale or on a larger scale. In terms of small scale production, this may be affected in, e.g. tissue culture flasks, and may be suitable for producing populations of cells for a given application and in the context of a specific condition, e.g. AML. One means of achieving large scale production in accordance with the method of the instant invention is via the use of a bioreactor.

Bioreactors are designed to provide a culture process that can deliver medium and nitrogen at controlled concentrations and rates that mimic nutrient concentrations and rates in vivo. Bioreactors are available commercially and employ a variety of types of culture technologies. Of the different bioreactors used for mammalian cell culture, most have been designed to allow for the production of high density cultures of a single cell type and as such find use in the present invention. In most instances, expansion and use of cultured leukaemia stem cells require the use of suitable micro carriers or beads for adhesion and proliferation of the undifferentiated stem cells. Those skilled in the art will be aware of the range of possible synthetic and biological carriers to allow efficient stem cell adhesion. Also included in the present invention is a means of culturing and expanding undifferentiated stem cells on biomaterial scaffolds and meshes of both synthetic and natural origin.

The present invention also provides a murine leukaemia stem cell line, wherein the cell line is deposited at CellBank Australia under the accession number CBA20150028 on 19 Nov. 2015.

In an aspect, the present invention provides a use of a mammalian leukaemia stem cell line produced according to the disclosed method or the murine leukaemia stem cell line deposited at CellBank Australia under the accession number CBA20150028 on 19 Nov. 2015 in a screening method to identify an agent with a pharmacological property, said method comprising exposing cells to an agent or agents; analysing the cells following exposure to an agent or agents; and identifying at least one agent having the pharmacological property.

The screening methods contemplated for use according to the present invention can be performed by any suitable means known to the person skilled in the art, wherein a plurality of different agents are simultaneously tested to identify at least one agent having a pharmacological property. For example, in vitro and/or in vivo assays can be used separately or in combination to identify drug candidates having the various pharmacological properties described herein. In one example embodiment, BET inhibitor resistance can be analyzed with a library. For example, the leukaemia stem cells of the present invention can be re-sensitized to a BET inhibitor by the overexpression of Dickopf Wnt signalling pathway inhibitor 1 (Dkk1), which also results in the differentiation of the leukaemia stem cells of the present invention into more mature leukaemia blast cells, thereafter a shRNA library of hundreds or thousands of shRNAs can be virally transduced into the re-sensitized leukaemia stem cells. The transduced leukaemia stem cells can be analyzed at a time point after the library of shRNAs have been transduced and resulting cells exposed to therapeutically relevant concentrations of a BET inhibitor. In this example, cells transduced with shRNA that remain viable after treatment with a BET inhibitor can be identified (e.g. by flow cytometry) as being resistant to a BET inhibitor, notwithstanding re-sensitization by overexpression of Dkk1 (FIG. 4).

In an embodiment, the agent is selected from the group consisting of small molecules, peptides, nucleic acids or biologics.

The term "small molecule" as used herein, refers to a composition that has a molecular weight of less than about 5 kDa and more preferably less than about 2 kDa. Small molecules can be, for example, nucleic acids, peptides, polypeptides, glycopeptides, peptidomimetics, carbohydrates, lipids, lipopolysaccharides, other organic or inorganic molecules, or combinations thereof.

The term "peptide" as used herein, means a short chain of amino acid monomers linked by peptide bonds. In some embodiments, the peptides for use according to the present invention can include about 2-50 amino acids. Reference to the term "about 2-50 amino acids" means 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids.

Screening of peptides can be performed to identify which peptides exhibit an activity for inhibiting a protein: protein interaction, inhibiting antagonism of a receptor, modulating an ion channel, inhibiting a signalling pathway, activating a signalling pathway, and/or inhibiting a protein: small molecule interaction. The activity of the peptide (e.g. the protein: protein interaction) can be associated with a disease or disorder, such as, e.g. a cancer.

The term "nucleic acid" as used herein, means any DNA or RNA polynucleotide. In some embodiments, the nucleic acids for use according to the present invention can include mediators of RNA interference. "RNA interference" or "RNAi" describes a mechanism of gene silencing that is based on degrading or otherwise preventing the translation of mRNA in a sequence specific manner that is dependent on small, non-coding RNA ~20 to 30-nucleotide (nt) in length. Three classes of small RNA can regulate genes by targeting transcripts in the cytoplasm: microRNAs (miRNAs), which are hairpin-derived RNAs with imperfect complementarity to targets and that cause translational repression; small interfering RNAs (siRNAs), which have perfect complementarity to targets and cause transcript degradation; and PIWI-interacting RNAs (piRNAs), which target transposon transcripts in animal germ lines. All three classes of small RNA share a common mode of action, the minimal effector is a ribonucleoprotein complex comprising an Argonaute family protein bound to a single-stranded ~20 to 30 nt RNA that exhibits specificity by base-pairing interactions with the gene target. In miRNA and siRNA pathways, this is known as the RNA-induced silencing complex (RISC) and it drives the silencing of a target mRNA by degradation and/or transcriptional repression.

Despite the similarities in processing of siRNA and miRNA, miRNAs are endogenously expressed from the genome, whereas siRNAs may be endogenous or arise from viral infection or other exogenous sources. Furthermore, siRNA duplexes feature perfect base-pairing, while miRNA helices contain mismatches and more extended terminal loops. In the cytoplasm, the processing pathways converge for endogenous miRNAs and for typically exogenous siRNAs. Both types of RNAi precursors are cleaved down by a Dicer enzyme to a dsRNA duplex of the appropriate size for loading onto an Argonaute protein. The resulting dsRNA is a duplex of 21- to 25-nt strands, with a 2-nt overhang at each 3' terminus and a phosphate group at each recessed 5' terminus. The bound duplex and Argonaute protein are subsequently loaded into the RISC complex in a strand dependent manner. One strand, the guide strand, of the duplex is bound to Argonaute to direct silencing and the other strand, the passenger strand, is discarded. The RISC performs cellular surveillance, binding single-stranded RNA (ssRNA) such as mRNA with complementarity to the guide strand. Guide strand nucleotides 2-6 constitute the seed sequence and initialize binding to the target.

piRNAs are produced and processed by a completely distinct pathway, known as the 'ping pong cycle'. Briefly, piRNA genomic clusters are transcribed to produce the piRNA precursors. In the cytoplasm, these precursors are cleaved into short 23-29-nt antisense piRNAs. These short, single stranded RNAs (ssRNAs) are loaded into PIWI family Argonaute proteins AUB and PIWI. The loaded AUB or PIWI proteins then target the mRNA of active transposons for cleavage to produce sense piRNAs. The sense piRNAs are loaded into the PIWI-specific Argonaute protein AGO3, which then directs cleavage of primary piRNA precursors and the subsequent production of more antisense piRNAs, completing the 'ping pong cycle'.

The RNAi molecules contemplated by the present invention should be understood to encompass all RNAi gene silencing mechanisms. The induction of RNAi to inhibit a target gene could be achieved by administering, in accordance with the method or use of the present invention, exogenous RNA oligonucleotides that can induce an RNAi mechanism. Reference to a "RNAi molecule" should therefore be understood as a reference to an RNA nucleic acid molecule that is double stranded or single stranded and is capable of effecting the induction of an RNAi mechanism to knock down the expression of a gene targeted or down regulating or preventing the onset of such a mechanism. In this regard, the subject RNAi molecule may be capable of directly mediating an RNAi mechanism, or it may require further processing. The subject RNAi molecule may be double stranded or single stranded. Examples of RNAi molecules that are suitable for use in the present application include, but are not limited to, long double stranded RNA (dsRNA), hairpin double stranded RNA (hairpin dsRNA), short interfering RNA (siRNA), short hairpin RNA (shRNA); microRNA (miRNA); and small temporal RNA (stRNA).

It will be appreciated that a person skilled in the art can determine the most suitable RNAi molecule for use in any given situation. For example, although it is preferable that the subject RNAi molecule exhibits 100% complementarity to its target nucleic acid molecule, the RNAi molecule may nevertheless exhibit some degree of mismatch to the extent that hybridization sufficient to induce an RNAi response in a sequence specific manner can be effected. Accordingly, it is preferred that the RNAi molecule of the present invention comprises at least 70%-100% sequence complementarity. Reference to "at least 70%-100%" means 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%.

The term "biologic" as used herein, means a naturally derived biological medical product. In some embodiments, the biologics for use according to the present invention can include vaccines, blood, or blood components, allergenics, somatic cells, gene therapies, tissues, recombinant therapeutic protein and living cells. Such biologics can be composed of sugars, proteins, nucleic acids or complex combinations of these substances.

As used herein, the term "pharmacological property" is a property of an agent that can be used to characterise the potential of an agent to elicit an effect on a target or subject. In an embodiment, the pharmacological property is selected from the group consisting of cell death, growth inhibition and senescence.

Methods for measuring cell death, growth inhibition and senescence would be known to persons skilled in the art. For example, methods for measuring cell viability generally rely on at least one of two features of viable cells, the presence of an intact plasma membrane and/or their metabolic activity. In vitro cell death is accompanied by the loss of plasma membrane integrity, which can be readily observed microscopically using vital dyes such as trypan blue. Alternatively, cell viability may also be assessed by measuring one or makers of metabolism such as key metabolites ATP and NADH, which are present in viable cells and depleted or absent from dead cells.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Unless defined otherwise, all technical and scientific terms used herein have the same meanings as commonly understood by one of ordinary skill in the art to which this invention belongs.

EXAMPLES

Aspects of certain embodiments of the present invention are further described by reference to the following non-limiting Examples.

Materials and Methods
Generation of Immortalised Primary Mouse HSPC Lines and Derivation of Clonal Cell Lines Initial generation of immortalised parental cell lines was achieved through magnetic bead selection (Miltenyi Biotec) of c-kit positive cells, obtained from whole bone marrow of male and female C57BL/6 mice, and subsequent retroviral transduction with either an MSCV-MLL-AF9-IRES-YFP or an MSCV-MLL-ENL construct.

To generate clonal resistant cell lines, the MLL-AFP bearing parental cell line was serially re-plated in cytokine supplemented methylcellulose (MethoCult M3434, StemCell Technologies) containing either vehicle (0.1% DMSO) or drug (400 nM I-BET 151). Individual vehicle-treated or resistant colonies were picked and transferred to liquid culture to generate clonal cell lines. Resistant cell lines were maintained continuously in drug while being incrementally exposed to increasing concentrations of drug (up to 1 µM I-BET 151). Vehicle-treated clones were also continuously maintained in 0.1% DMSO and passaged in identical fashion. The parental cell line was continuously maintained with no exposure to vehicle or drug.

Similarly, to generate resistant cell lines, the MLL-ENL-bearing parental cell line was serially re-plated in cytokine-supplemented methylcellulose (MethoCult M3434, StemCell Technologies) containing either vehicle (0.1% DMSO) or drug (400 nM I-BET 151). Cells growing in each plate were then washed and transferred to liquid culture to generate cell lines. Resistant cell lines were maintained continuously in drug while being incrementally exposed to increasing concentrations of drug (up to 1 µM I-BET 151). Vehicle-treated clones were also continuously maintained in 0.1% DMSO and passaged in identical fashion. The parental cell line was continuously maintained with no exposure to vehicle or drug.

Cell Culture

Primary murine haematopoietic progenitors and derived cell lines were grown in RPMI-1640 supplemented with murine IL-3 (10 ng/mL), 20% foetal calf serum, penicillin (100 units/mL), streptomycin (100 µg/mL), amphotericin B (250 ng/mL) and gentamycin (50 µg/mL). Cell lines were routinely tested for *mycoplasma* contamination by PCR. Primary human leukaemia cells were grown in the presence of IL3 (10 ng/mL), IL6 (10 ng/mL) and SCF (50 ng/mL). Cells were incubated at 37° C. and 5% $CO_2$.

Cell Proliferation Assays

For dose-response assays, serial dilutions of I-BET 151, JQ1 or pyrvinium were further diluted in media prior to addition to 96-well plates seeded with between $5 \times 10^3$ and $1 \times 10^4$ cells per well to obtain a 0.1% DMSO final concentration. Following 72 hour incubation, resazurin was added to each well and plates were further incubated for 3 hours. Fluorescence was then read at 560 nm/590 nm on a Cytation 3 Imaging Reader (BioTek). Cell counts were performed using a haemocytometer. Determination of in vitro synergy in proliferation assays was undertaken according to the method of Zhao et al. (2014, *Journal of molecular screening*, 19: 817-821).

Clonogenic Assays in Methylcellulose

Clonogenic potential was assessed through colony growth of derived cell lines plated in cytokine supplemented methylcellulose (Methocult M3434, Stemcell Technologies). Derived vehicle treated and resistant cell lines were plated in duplicate at a cell dose of $2 \times 10^2$ per plate in the presence of vehicle (0.1% DMSO) or drug (1 µM I-BET 151). Gr1−/CD11b− and Gr1+/CD11b+ fractions of resistant cell lines were plated in duplicate following FACS sorting at a cell dose of between $2 \times 10^2$ and $2 \times 10^3$ cells per plate. FACS isolated L-GMP populations from whole mouse bone marrow following primary syngeneic transplant of vehicle treated clones were plated in duplicate at a cell dose of between $2 \times 10^2$ and $2 \times 10^3$ cells per plate in the presence of vehicle (0.1% DMSO) or drug (1 µM I-BET 151). Cells were incubated at 37° C. and 5% $CO_2$ for 7 to 10 days at which time colonies were counted.

Flow Cytometric Analyses

Cell apoptosis was assessed using APC conjugated Annexin V (550475, BD Biosciences) and propidium iodide (PI) (P4864, Sigma-Aldrich) staining according to manufacturer's instructions.

For cell cycle analysis, cells were fixed overnight at −20° C. in 70% EtOH/PBS. Prior to flow cytometry analysis, cells were incubated at 37° C. for 30 minutes in PI staining solution (0.02 mg/mL PI, 0.05% v/v Triton-X in PBS, supplemented with DNase-free RNase A (19101, Qiagen) or incubated at room temperature for 10 minutes with 4',6-diamidino-2-phenylindole (DAPI) staining solution (1 µg/ml DAPI, 0.05% v/v Triton-X in PBS).

Immunophenotype assessment for markers of committed differentiation was undertaken through staining with Alexa Fluor 700 anti-Gr-1 (108422, BioLegend) and Brilliant Violet 605 anti-CD11b (101237, BioLegend). Assessment of L-GMP populations was undertaken through staining with eFluor 660 anti-CD34 (50-0341-82, eBioscience), biotin lineage antibody cocktail (120-001-547, Miltenyi Biotec), PerCP/Cy5.5 anti-CD16/32 (101324, BioLegend), APC/Cy7 anti-CD117 (105826, BioLegend) and Pacific Blue anti-Ly- 6A (122520, BioLegend) followed by secondary staining with V500 streptavidin (561419, BD Biosciences). Assessment of leukemic LMPP and GMP populations in patient derived xenografts was undertaken through staining with APC/Cy7 anti-mouse CD45.1 (110716, Biolegend), eFluor 450 anti-mouse Ter119 (48-5921-82, eBioscience), FITC anti-human CD45 (11-9459-42, eBioscience), BV711 anti-human CD38 (563965, BD Biosciences), PE anti-human CD90 (561970, BD Biosciences), PE-Cy5 anti-human CD123 (15-1239-41, eBioscience), PerCP-Cy5.5 anti-human CD45RA (45-0458-42), biotin anti-human CD3 (555338, BD Biosciences), biotin anti-human CD19 (555411, BD Biosciences), PE-Cy7 anti-human CD33 (333946, BD Biosciences) and APC anti-human CD34 (555824, BD Biosciences) followed by secondary staining with V500 streptavidin (561419, BD Biosciences).

PI or DAPI was used as a viability dye to ensure that immunophenotyping analyses were performed on viable cells. Appropriate unstained, single stained and fluorescence minus one controls were used to determine background staining and compensation in each channel.

Flow cytometry analyses were performed on the LSR-Fortessa X-20 flow cytometer (BD Biosciences) and all data analysed with FlowJo software (vX.0.7, Tree Star). Cell sorting was performed on a FACSAria Fusion flow sorter (BD Biosciences).

RNAi Studies shRNAs were cloned into TtRMPVIR (27995, Addgene). For competitive proliferation assays, transduced cells were sorted for shRNA-containing (Venus+/YFP+) and non shRNA-containing (YFP+ only) populations and recombined at a 1:1 ratio. Following this, cells were cultured with 1 mg/mL doxycycline to induce shRNA expression. The proportion of shRNA-expressing (dsRED+/Venus+/YFP+) cells were determined by flow cytometric analysis and followed over time. Knockdown efficiency of shRNA-expressing and non shRNA-containing cells was assessed following 48 to 72 hours of doxycycline exposure by qRT-PCR and immunoblotting.

| shRNA | Target | Sequence |
|---|---|---|
| #851 | BRD2 | CGGATTATCACAAAATTAT (SEQ ID NO: 1) |
| #498 | BRD4 | ACTATGTTTACAAATTGTT (SEQ ID NO: 2) |
| #499 | BRD3/4 | AGGACTTCAACACTATGTT (SEQ ID NO: 3) |
| #500 | BRD4 | AGCAGAACAAACCAAAGAA (SEQ ID NO: 4) | shRNA directed against APC were cloned into LMN-mirE-mCherry. The proportion of shRNA-expressing (mCherry+) cells were determined by flow cytometric analysis following treatment with vehicle (0.1% DMSO) or I-BET 151 and followed over time. Selective advantage consequent to shRNA expression results in enrichment of mCherry+ cells. Knockdown efficiency of APC in shRNA-expressing cells was assessed following FACS of mCherry positive cells. shRNAs directed against APC were a kind gift from Johannes Zuber (Rathert et al. 2015, *Nature*, 525: 543-547).

qRT-PCR mRNA was prepared using the Qiagen RNeasy kit and cDNA synthesis was performed using SuperScript VILO kit (Life Technologies) as per manufacturer's instructions. Quantitative PCR analysis was undertaken on an Applied Biosystems StepOnePlus System with SYBR green reagents (Life Technologies).

For analysis of murine cell line samples, expression levels were determined using the ΔCT method and normalised to beta-2-microglobulin (B2M) and/or GAPDH. Differences in expression were assessed using a one-sided t-test for statistical significance. Assessment of expression changes associated with I-BET 151 treatment occurred at 6 hours following treatment with 1 μM I-BET 151. The following primer pairs were used:

Mouse

| Amplicon | Forward primer | Reverse primer |
|---|---|---|
| APC | GGAGTGGCAGAAAGCAACAC (SEQ ID NO: 5) | AAACACTGGCTGTTTCGTGA (SEQ ID NO: 6) |
| B2M | GAGCCCAAGACCGTCTACTG (SEQ ID NO: 7) | GCTATTTCTTTCTGCGTGCAT (SEQ ID NO: 8) |
| BRD2 | TGGGCTGCCTCAGAATGTAT (SEQ ID NO: 9) | CCAGTGTCTGTGCCATTAGG (SEQ ID NO: 10) |
| BRD3 | GCCAGTGAGTGTATGCAGGA (SEQ ID NO: 11) | GCCTGGGCCATTAGCACTAT (SEQ ID NO: 12) |
| BRD4 | TCTGCACGACTACTGTGACA (SEQ ID NO: 13) | GGCATCTCTGTACTCTCGGG (SEQ ID NO: 14) |
| CCND2 | CAAGCCACCACCCCTACA (SEQ ID NO: 15) | TTGCCGCCCGAATGG (SEQ ID NO: 16) |
| DKK1 | CTGCATGAGGCACGCTATGT (SEQ ID NO: 17) | AGGAAAATGGCTGTGGTCAG (SEQ ID NO: 18) |
| DVL1 | ATCACACGCACCAGCTCTTC (SEQ ID NO: 19) | GGACAATGGCACTCATGTCA (SEQ ID NO: 20) |
| FZD5 | GGCTACAACCTGACGCACAT (SEQ ID NO: 21) | CAGAATTGGTGCACCTCCAG (SEQ ID NO: 22) |
| GAPDH | GGTGCTGAGTATGTCGTGGA (SEQ ID NO: 23) | CGGAGATGATGACCCTTTTG (SEQ ID NO: 24) |
| GSK3β | TTGGAGCCACTGATTACACG (SEQ ID NO: 25) | CCAACTGATCCACACCACTG (SEQ ID NO: 26) |
| MYC | TGAGCCCCTAGTGCTGCAT (SEQ ID NO: 27) | AGCCCGACTCCGACCTCTT (SEQ ID NO: 28) |

For determination of baseline WNT/β-catenin pathway and target gene expression in primary human AML samples, expression relative to the mean of all samples was determined using the ΔCT method and normalised to GAPDH and actin. The following primers were used:

Human

| Amplicon | Forward primer | Reverse primer |
|---|---|---|
| AXIN2 | CGGACAGCAGTGTAGATGGA (SEQ ID NO: 29) | CTTCACACTGCGATGCATTT (SEQ ID NO: 30) |
| CCND1 | GCTGTGCATCTACACCGACA (SEQ ID NO: 31) | CCACTTGAGCTTGTTCACCA (SEQ ID NO: 32) |
| CTNNB1 | GACCACAAGCAGAGTGCTGA (SEQ ID NO: 33) | CTTGCATTCCACCAGCTTCT (SEQ ID NO: 34) |
| FZD5 | TTCCTGTCAGCCTGCTACCT (SEQ ID NO: 35) | CGTAGTGGATGTGGTTGTGC (SEQ ID NO: 36) |

-continued

| Amplicon | Forward primer | Reverse primer |
|---|---|---|
| MYC | CTGGTGCTCCATGAGGAGA (SEQ ID NO: 37) | CCTGCCTCTTTTCCACAGAA (SEQ ID NO: 38) |
| TCF4 | ATGGCAAATAGAGGAAGCGG (SEQ ID NO: 39) | TGGAGAATAGATCGAAGCAAG (SEQ ID NO: 40) |
| ACTIN | TTCAACACCCCAGCCATGT (SEQ ID NO: 41) | GCCAGTGGTACGGCCAGA (SEQ ID NO: 42) |
| GAPDH | ACGGGAAGCTTGTCATCAAT (SEQ ID NO: 43) | TGGACTCCACGACGTACTCA (SEQ ID NO: 44) |

Immunoblotting

Whole cell lysates were mixed with Laemmli SDS sample buffer, separated via SDS-PAGE and transferred to PVDF membranes (Millipore). Membranes were then sequentially incubated with primary antibodies (see antibodies) and secondary antibodies conjugated with horseradish peroxidase (Invitrogen). Membranes were then incubated with ECL (GE Healthcare) and proteins detected by exposure to x-ray film.

Mouse Tissue Sample Preparation

Peripheral blood samples were collected in EDTA-treated tubes (Sarstedt) and counted using a XP-100 analyser (Sysmex). Single cell cytospins and blood smears were stained with the Rapid Romanowsky Staining Kit (Thermo Fisher Scientific). Bone marrow cells were isolated by flushing both femurs and tibias with cold PBS. Prior to flow cytometry, red blood cells were lysed in red blood cell lysis buffer (Sigma).

Examination of Drug Efflux and Metabolism by Quantitative Mass Spectrometry

Between $2\times10^5$ and $3\times10^5$ cells per well were seeded in 24-well plates and treated with vehicle (0.1% DMSO) or 600 nM I-BET 151. Following 48 hours, cells were harvested by centrifugation, washed twice in ice cold PBS and lysed in M-PER buffer (78501, Thermo Scientific). Base media, supernatant, wash and cell lysates were quenched with 5% acetonitrile (aq) containing labetalol at 62.5 ng/mL as the internal standard. These samples, in addition to serial dilutions of I-BET 151 used to generate standard curves, were then analysed by mass spectrometry.

HPLC-mass spectrometry apparatus and conditions: The HPLC system was an integrated CTC PAL auto sampler (LEAP technologies), Jasco XTC pumps (Jasco). The HPLC analytical column was an ACE 2 C18 30 mm×2.1 mm (Advanced Chromatography Technologies) maintained at 40° C. The mobile phase solvents were water containing 0.1% formic acid and acetonitrile containing 0.1% formic acid. A gradient ran from 5% to 95% ACN+0.1% formic acid up to 1.3 minutes, held for 0.1 minutes and returning to the starting conditions over 0.05 minutes then held to 1.5 minutes at a flow rate of 1 mL/min. A divert valve was utilised so the first 0.4 min and final 0.2 minutes of flow were diverted to waste.

Mass spectromic detection was by an API 4000 triple quadrupole instrument (AB Sciex) using multiple reaction monitoring (MRM). Ions were generated in positive ionization mode using an electrospray interface. The ionspray voltage was set at 4000 V and the source temperature was set at 600° C. For collision dissociation, nitrogen was used as the collision gas. The MRM of the mass transitions for I-BET 151 (m/z 416.17 to 311.10), and Labetalol (m/z 329.19 to 162.00), were used for data acquisition.

Data was collected and analysed using Analyst 1.4.2 (AB Sciex), for quantification, area ratios (between analyte/internal standard) were used to construct a standard line, using weighted ($1/x^2$) linear least squared regression, and results extrapolated the area ratio of samples from this standard line.

Murine Models of Leukaemia

Primary syngeneic transplantation studies of stably growing derived vehicle treated or resistant cell lines in limit dilution analyses were performed with intravenous injection of between 10 to $2\times10^6$ cells per mouse.

Serial syngeneic transplantation studies of drug efficacy, generation of in vivo resistance and limit dilution analyses were performed with intravenous injection of between 10 to $2.5\times10^6$ cells per mouse obtained from bone marrow or spleen. Treatment with vehicle or I-BET 151 at 20-30 mg/kg began between days 9-13. Pyrvinium, alone or in combination with I-BET 151, was delivered between days 9 & 26.

Following stable retroviral transduction of resistant cell lines with a DKK1 containing construct, $5\times10^6$ cells per mouse were injected intravenously in primary syngeneic transplants. Treatment with vehicle or I-BET 151 at 20 mg/kg began at day 16.

Syngeneic transplantation studies were performed in C57BL/6 mice (wild type or expressing Ptprc$^a$). All mice were 6-10 weeks old at the time of sub-lethal irradiation (300 cGy) and intravenous cell injection. Treatment with vehicle, I-BET 151 or pyrvinium was commenced following engraftment of leukaemia as determined by >1% YFP expression in peripheral blood in the majority of mice. Mice were randomly assigned treatment groups; treatment administration was not blinded. Sample sizes were determined according to the resource equation method. Differences in Kaplan-Meier survival curves were analysed using the log-rank statistic.

Patient derived xenograft studies were performed in NOD SCID gamma (NSG) mice. All mice were 6-10 weeks old at the time of sub-lethal irradiation (200 cGy) and intravenous cell injection of $1\times10^5$ to $5\times10^5$ cells per mouse. Treatment with vehicle or I-BET 151 at 10 mg/kg for a 2 week period began upon detection of >1% circulating human CD45$^+$ cells in mouse peripheral blood at week 14. Treatment cohorts were matched for transplant generation.

I-BET 151 was dissolved in normal saline containing 5% (v/v) DMSO and 10% (w/v) Kleptose HPB. I-BET 151 was delivered daily (5 days on, 2 days off) by intra-peritoneal (IP) injection (10 mL/kg) with dose reduction of I-BET 151 undertaken if evidence of drug intolerance was present. Pyrvinium was dissolved in normal saline containing 15% (v/v) DMSO and delivered daily by IP injection (10 mL/kg). Dosing of pyrvinium was commenced at 0.1 mg/kg and escalated in 0.1 mg/kg increments every second dose to a maximal dose of 0.5 mg/kg.

All mice were kept in a pathogen free animal facility, inspected daily and sacrificed upon signs of distress/disease. All experiments were conducted under either UK home office regulations or institutional animal ethics review board in Australia. Statistical analysis of limit dilutions was undertaken according to the method of Hu and Smyth (*Journal of Immunological Methods,* 2009, 347: 70-78).

Exome Capture Sequencing

DNA was extracted from cell lines using the DNeasy blood and tissue kit (Qiagen), and quantified using the Qubit dsDNA HS Assay (Life Technologies) prior to fragmentation to a peak size of approximately 200 bp using the focal acoustic device, SonoLab S2 (Covaris). Library preparations were performed using the SureSelect$^{XT}$ Target Enrichment System for Illumina Paired-End Sequencing Library protocol (Agilent Technologies) with the SureSelect$^{XT}$ Mouse All Exon Kit for the capture process (Agilent Technologies). The quality of libraries submitted for sequencing was assessed using the High Sensitivity DNA assay on the 2100 bioanalyzer (Agilent technologies, Santa Clara, Calif.). Libraries were quantified with qPCR, normalised and pooled to 2 nM before sequencing with paired end 100 bp reads using standard protocols on the HiSeq2500 (Illumina).

The Fastq files generated by sequencing were aligned to the mm10 mouse reference genome using bwa (Li & Fast, 2009, *Bioinformatics*, 25: 1754-1760). Copy number variation was analysed using ADTEx (Amarasinghe & Halgamuge, 2013, *BMC Bioinformatics*, 14 Suppl 2 (S2)) to compare the depth of coverage in resistant and vehicle treated clones with the parental cell line. Variant calling was performed with VarScan2 (Koboldt et al. 2012, *Genome Research*, 22: 568-576), MuTect (Cibulskis et al. 2013, *Nature Biotechnology*, 31: 213-219) and GATK HaplotypeCaller (McKenna et al. 2010, *Genome Research*, 20: 1297-1303). The Ensembl Variant Effect Predictor (VEP) (McLaren et al. 2010, *Bioinformatics*, 26: 2069-2070) was used to predict the functional effect of the identified variants.

Mutations detected by at least two variant callers were further analysed for shared mutations between cell lines and mutation spectrum. Genomic regions with coverage of at least 8 reads in all libraries were analysed for the frequency of mutations. Coding exonic, UTRs and intronic regions were obtained from the UCSC Table Browser (Karolchik et al. 2004, *Nucleic Acids Research*, 32: D493-496). Upstream regions were defined as 1000 bp upstream of genes, downstream regions were defined as 1000 bp downstream of genes, and intergenic regions were over 1000 bp from genes.

Chromatin Immunoprecipitation Assay, Real-Time PCR and Sequencing Analysis

Cells were cross-linked with 1% formaldehyde for 15 minutes at room temperature and cross-linking stopped by the addition of 0.125 M glycine. Cells were then lysed in 1% SDS, 10 mM EDTA, 50 mM Tris-HCl pH 8.0 and protease inhibitors. Lysates were sonicated in a Covaris ultrasonicator to achieve a mean DNA fragment size of 500 bp. Immunoprecipitation (see antibodies) was performed for a minimum of 12 hours at 4° C. in modified RIPA buffer (1% Triton X, 0.1% deoxycholate, 90 mM NaCl, 10 mM Tris-HCl pH 8.0 and protease inhibitors). An equal volume of protein A and G magnetic beads (Life Technologies) were used to bind the antibody and associated chromatin. Reverse crosslinking of DNA was followed by DNA purification using QIAquick PCR purification kits (Qiagen). Immunoprecipitated DNA was analysed on an Applied Biosystems StepOnePlus System with SYBR green reagents. The following primer pairs were used in the analysis:

ChIP Primers

| Amplicon | Forward primer | Reverse primer |
|---|---|---|
| MYC TSS | GTCACCTTTACCCCGACTCA (SEQ ID NO: 45) | TCCAGGCACATCTCAGTTTG (SEQ ID NO: 46) |
| MYC enhancer | TCTTTGATGGGCTCAATGGT (SEQ ID NO: 47) | TTCCCTTCACCTGATGAACC (SEQ ID NO: 48) |

For sequencing analysis of immunoprecipitated DNA, DNA was quantified using the Qubit dsDNA HS Assay (Life Technologies). Library preparations were performed using the standard ThruPLEXTM-FD Prep Kit protocol (Rubicon Genomics) and size selected for 200-400 bp using the Pippen Prep (Sage Science Inc.). Fragment sizes were established using either the High Sensitivity DNA assay or the DNA 1000 kit and 2100 bioanalyzer (Agilent Technologies). Libraries were quantified with qPCR, normalised and pooled to 2 nM before sequencing with single end 50 bp reads using standard protocols on the HiSeq2500 (Illumina). The Fastq files generated by sequencing were aligned to the mm10 mouse reference genome using bwa (Li & Durbin, 2009, *Bioinformatics*, 25: 1754-1760). Peak-calling was performed using MACS2 (Zhang et al. 2008, *Genome Biology*, 9: R137) with default parameters and the input library as control. Profiles and heat maps of reads and MACS peaks in the 5 kb around TSS were generated with Genomic Tools (Tsirigos et al. 2012, *Bioinformatics*, 28: 282-283).

Expression Analysis by Microarray and RNA-Sequencing

RNA was prepared using the Qiagen RNeasy kit. For microarray analysis, RNA was hybridised to Illumina MouseWG-6 v2 Expression BeadChips. Gene expression data were processed using the lumi package in R. Probe sets were filtered to remove those where the detection p-value (representing the probability that the expression is above the background of the negative control probe) was greater than 0.05 in at least one sample. Expression data was background corrected and quantile normalised. Normalisation and inference of differential expression were performed using limma (Smyth in *Bioinformatics and Computational Biology Solutions using R and Bioconductor* (ed. Carey et al. 2005)). Correction for multiple testing was performed using the method of Benjamini and Hochberg (1995, *Journal of the Royal Statistical Society Series B*, 57: 289-300). Genes with a false discovery rate below 0.05 and a fold-change greater than 2 were considered significantly differentially expressed. For genes with multiple probe sets, only the probe set with the highest average expression across samples was used.

For RNA sequencing analysis, RNA concentration was quantified with the NanoDrop spectrophotometer (Thermo Scientific). The integrity was established using the RNA 6000 kit and 2100 bioanalyzer (Agilent Technologies). Library preparations were performed using the standard TruSeq RNA Sample Preparation protocol (Illumina) with fragment sizes established using the DNA 1000 kit and 2100 bioanalyzer (Agilent Technologies). Libraries were quantified with qPCR, normalised and pooled to 2 nM before sequencing with paired-end 50 bp reads using standard protocols on an Illumina HiSeq2500.

Reads were aligned to the mouse genome (Ensembl Release 75, February 2014) using Subread (Liao et al. 2013, *Nucleic Acids Research*, 41: e108) and assigned to genes using feature Counts (Liao et al. 2014, *Bioinformatics*, 30: 923-930). Differential expression was inferred using limma/voom[45]. Correction for multiple testing using the Benjamini-Hochberg method was performed. Genes with a false discovery rate below 0.05 and a fold-change greater than 2 were considered significantly differentially expressed.

Gene set enrichments were determined using ROAST (Wu et al. 2010, *Bioinformatics*, 26: 2176-2182). ROAST tests for up- or down-regulation of genes in a given pathway were performed on cell lines either stably maintained in vehicle or I-BET 151. P-values were corrected for multiple testing using the method of Benjamini and Hochberg. Gene sets were obtained from MSigDB (Subramanian et al. 2005, PNAS, 102: 15545-15550) and curated. Human Entrez accessions from the downloaded gene sets were converted into mouse accessions using ortholog information from the Mouse Genome Database (MGD) at the Mouse Genome Informatics website, The Jackson Laboratory, Bar Harbor, Me. World Wide Web (URL: http://www.informatics.jax.org). [Retrieved June 2014]. ROAST tests were performed to assess for an enrichment of a LGMP gene expression signature (GSE4416) (Krivtsov et al. 2006 Nature 442: 818-822) and a LGMP derived from HSC signature (GSE18483) (Krivtsov et al. 2013 Leukemia 27: 852-860) in the I-BET resistant compared with vehicle cell lines. The gene expression program associated with human leukemia stem cells was obtained from GSE30375 (Eppert et al. 2011 Nature Medicine 17: 1086-1093) and analyzed with LIMMA (Ritchie et al. 2015 Nucleic Acids Research 43(7): e47). Gene expression of LSC was compared with LPC and genes upregulated in LSC were analyzed for an enrichment of the Wnt/β-catenin pathway using ROAST.

GSEA Terms

| | |
|---|---|
| WNT/beta-catenin | ST_WNT_BETA_CATENIN_PATHWAY |
| JAK/STAT | KEGG_JAK_STAT_SIGNALING_PATHWAY |
| PI3K/AKT/mTOR | REACTOME_PI3K_AKT_ACTIVATION |
| nF-kB | REACTOME_ACTIVATION_OF_NF_KAPPAB_IN_B_CELLS |
| RAS/ERK/MAPK | KEGG_MAPK_SIGNALING_PATHWAY |
| NOTCH | KEGG_NOTCH_SIGNALING_PATHWAY |
| hippo | REACTOME_SIGNALING_BY_HIPPO |
| hedgehog | KEGG_HEDGEHOG_SIGNALING_PATHWAY |
| TGP-beta | KEGG_TGF_BETA_SIGNALING_PATHWAY |

Antibodies

The following antibodies were used in ChIP and immunoblotting assays: anti-BRD2 (A302-583A, Bethyl Labs), anti-BRD3 (A302-368A, Bethyl Labs), anti-BRD4 (A301-985A, Bethyl Labs and ab128874, abcam), anti-H3K27ac (ab4729, abcam), anti-β-catenin (610154, BD Biosciences), anti-c-MYC (9402S, Cell Signalling Technology), anti-β-actin (A1978, Sigma-Aldrich) and anti-HSP60 (sc-13966, Santa Cruz Biotechnology).

Results

Murine HSPCs isolated from whole bone marrow were transduced with MLL-AF9 to establish a model of AML. Following a selection period in cytokine-supplemented methylcellulose in the presence of dimethylsulphoxide (DMSO; vehicle) or I-BET at the $IC_{40}$ of these cells (400 nM), individual blast colonies were isolated, each derived from a single cell, to generate 4 independent vehicle treated and 5 independent I-BET resistant cell lines (FIG. 1A). The selection pressure on I-BET resistant clones was sequentially increased to establish clones stably growing at various concentrations including those greater than the $IC_{90}$ of the parental and vehicle treated cells (FIGS. 1A and B).

Figure 1C:
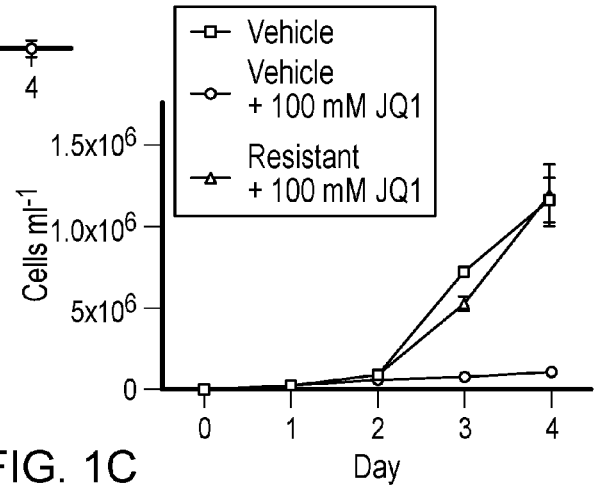

Resistance to I-BET also confers cross-resistance to the chemically distinct BET inhibitor JQ1 (FIG. 1C). Furthermore, direct comparison of these cell lines demonstrated that whilst vehicle treated cells remained exquisitely sensitive to I-BET mediated suppression of clonogenic capacity, induction of apoptosis and cell cycle arrest; resistant cells were now impervious to these established phenotypic responses at levels that positively correlated with the degree of selective pressure applied (FIG. 1D-F). High content shRNA screens in this AML model previously identified BRD4 as the major therapeutic target of BET inhibitors (Zuber et al. 2011 Nature 478: 524-528). Using an inducible shRNA system, these findings were replicated in vehicle-treated clones; however BET inhibitor resistant clones were significantly less susceptible to genetic depletion of BRD4 (FIG. 1G).

I-BET leads to a significant survival advantage in this AML model (FIG. 1H). In contrast, this survival advantage is abrogated following an identical treatment strategy in recipients of resistant cells (FIG. 1I). Together, these findings establish a robust model of BET inhibitor resistance in vitro and in vivo and show that resistant cells are refractory to either chemical or genetic perturbation of BRD4.

Figure 2A:
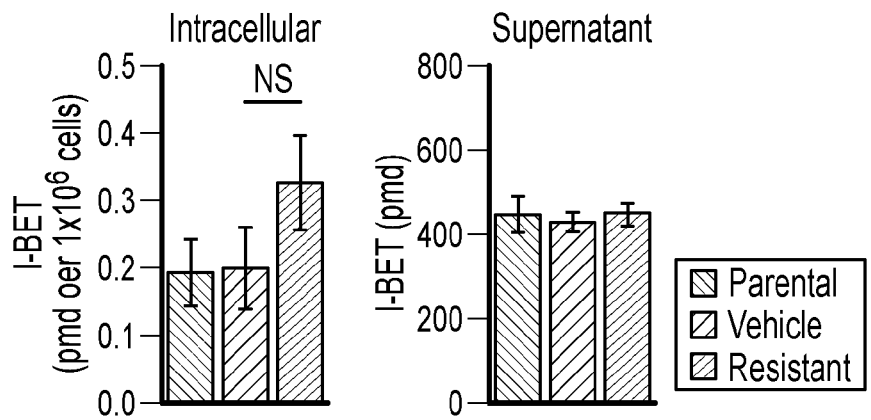
FIG. 2A-2H shows that BET inhibitor resistance arises from the leukemic stem cell compartment. (A) A graphical representation of parental, vehicle and resistant cells (x-axis) against I-BET concentration (y-axis; pmol per $1\times10^6$ cells) showing that BET inhibitor resistance is not mediated by increased drug efflux as there is no significance difference in the amount of intracellular and extracellular drug (NS; two-tailed Student's t-test). (B) A graphical representation of number of CD11b positive cells ($\times10^n$) against the number of Gr1 positive cells ($\times10^n$) showing that resistant clones demonstrate an immature immunophenotype (Gr1$^-$/CD11b$^-$). (C) A graphical representation of the clonogenic capacity of Gr1$^+$/CD11b$^+$ compared to Gr1$^-$/CD11b$^-$ cells showing that Gr1$^-$/CD11b$^-$ cells demonstrate significantly increased blast colony forming potential (P VALUE). (D) A graphical representation of time (days; x-axis) against survival (%; y-axis) showing that primary transplantation of I-BET-resistant cells results in considerably shorter leukaemia latency. (E) A graphical representation of cell dose ($\times10n$; x-axis) against non-responding cells (log fraction; y-axis) showing that I-BET-resistant cells are enriched for LSC potential. (F) A graphical representation of transplanted cells (x-axis) against L-GMP frequency (%; y-axis) showing that I-BET resistance emerges in vivo from an L-GMP/LSC population. (G) A graphical representation of LMPP, GMP and CD34+ cells (x-axis) against hCD45 expression (%; y-axis) showing that I-BET treatment enriches for the leukemic LMPP population. (H) A graphical representation of resistant and sensitive cells (x-axis) against the number of colonies formed (y-axis) showing that I-BET-naïve L-GMPs do not exhibit intrinsic resistance to I-BET.

Major mechanisms of drug resistance include reduced drug influx or increased drug efflux. Quantitative mass spectrometry was performed to assess if drug influx or efflux was mediating BET-inhibitor resistance. No significant difference in the amount of intracellular or extracellular drug was observed (FIG. 2A).

Figure 2B:
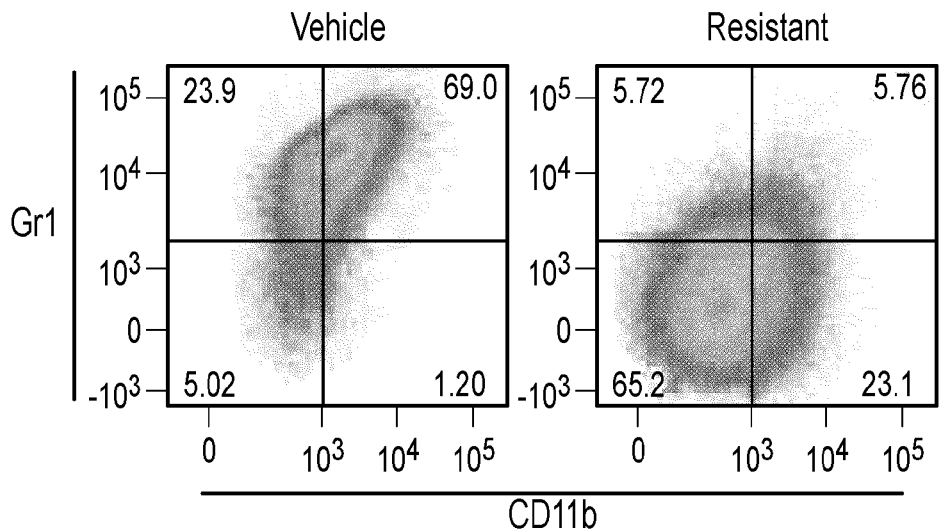
Figure 2C:
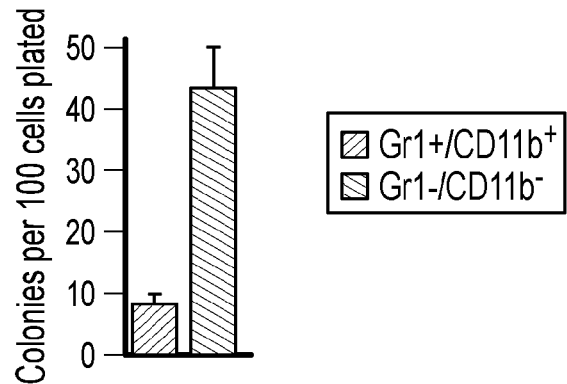

Immunophenotypic characterisation of sensitive and resistant cells revealed marked differences in expression of lineage markers Gr1 and CD11b (FIG. 2B). LSC potential primarily resides in the more immature, lineage negative (Lin–, Sca–, cKit+, CD34+, FcγRII/RIII+) leukemic granulocyte-macrophage progenitor (L-GMP) population, raising the possibility that BET inhibitor resistant cells are enriched for LSCs (Krivtsov et al. 2006, Nature, 442: 818-822; Wang et al. 2010, Science, 327: 1650-1653; Krivtsov et al. 2013, Leukemia, 27: 852-860). Consistent with this notion, a significant increase in blast colony forming potential of the Lin– (Gr1–/CD11b–) population and a marked increase in L-GMP cells was observed in the resistant population prior to primary transplantation (FIG. 2C).

Figure 2D:
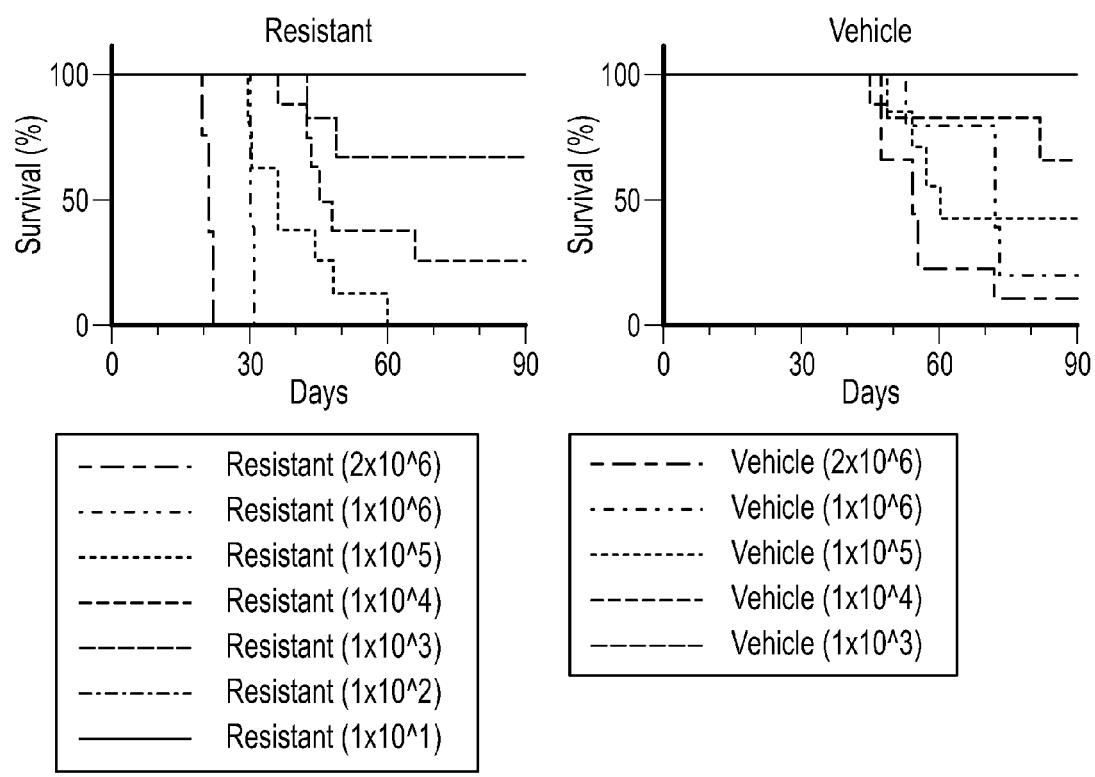
Figures 2E, 2F:
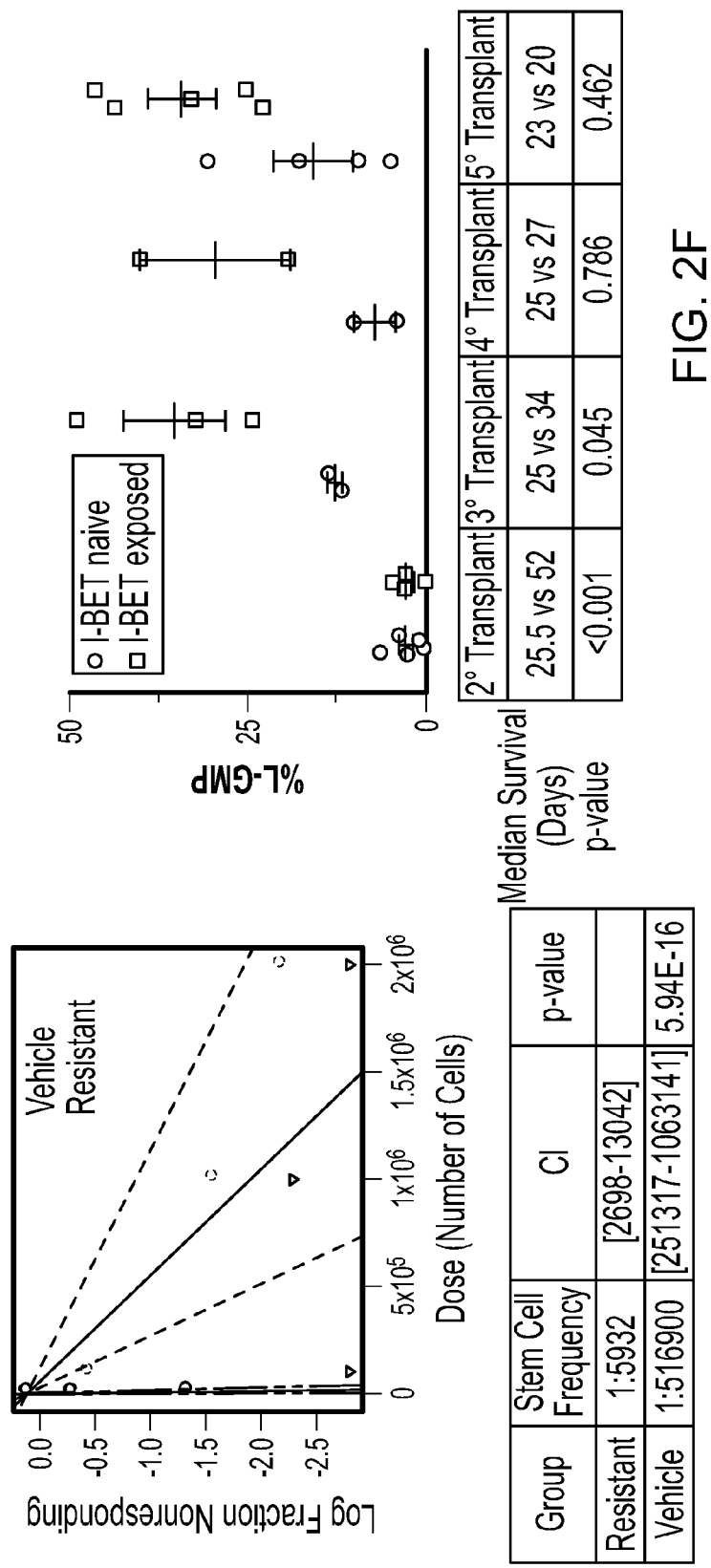

Whilst primary transplantation of vehicle treated cells paralleled the natural history of this AML model, remarkably, primary transplantation of I-BET resistant cells resulted in considerably shorter leukaemia latency (FIG. 2D). Moreover, limiting dilution transplantation analyses (LDA) confirm that I-BET resistant cells were markedly enriched for LSC potential (FIGS. 2D and E). To assess the relevance of these findings to resistance that emerges in vivo following sustained exposure to I-BET we derived an independent in vivo model of I-BET resistance, which shows that in vivo BET-inhibitor resistance also emerges from an L-GMP/LSC population (FIG. 2F). Importantly, these I-BET resistant AML cells have a functional LSC frequency of approximately 1:6; this is virtually identical to what has previously been reported for a purified L-GMP population (Krivtsov et al. 2006, Nature, 442: 818-822).

Figure 2G:
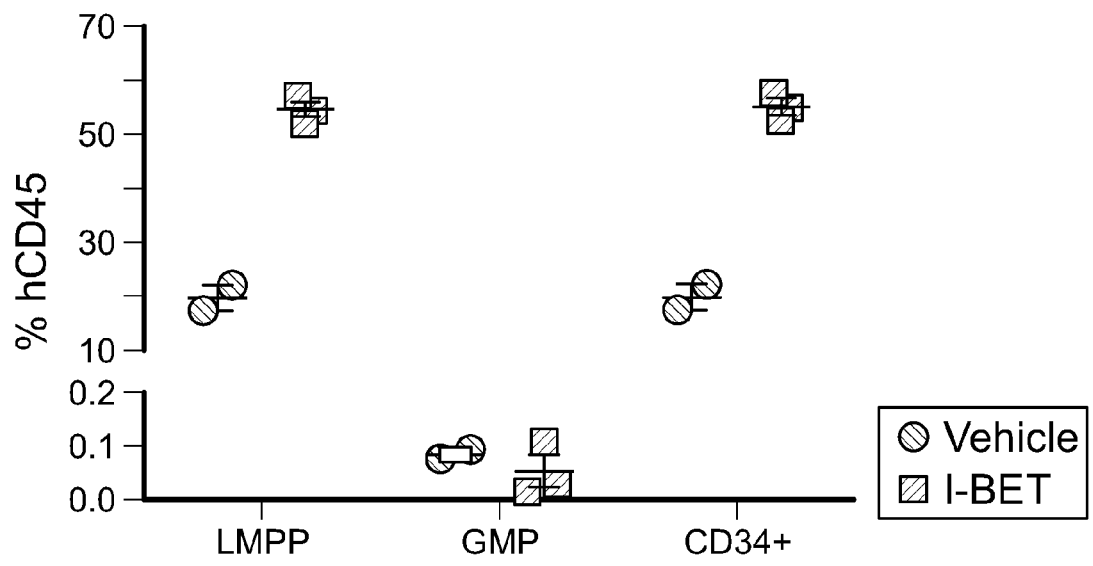

To extend these findings into primary patient samples we treated a patient derived xenograft (PDX) model of AML with I-BET. Whilst the immunophenotype of human AML LSC can be variable, several PDX models have shown that LSCs are enriched within CD34+ cells (Eppert et al. 2011, Nature Medicine, 17: 1086-1093), which immunophenotypically parallel GMPs or lymphoid-primed multipotent progenitors (LMPPs) (Goardon et al. 2011, Cancer Cell, 19: 138-152). Consistent with the data from our murine AML models, we find that I-BET treatment enriches for the leukemic LMPP population (FIG. 2G).

Figure 2H:
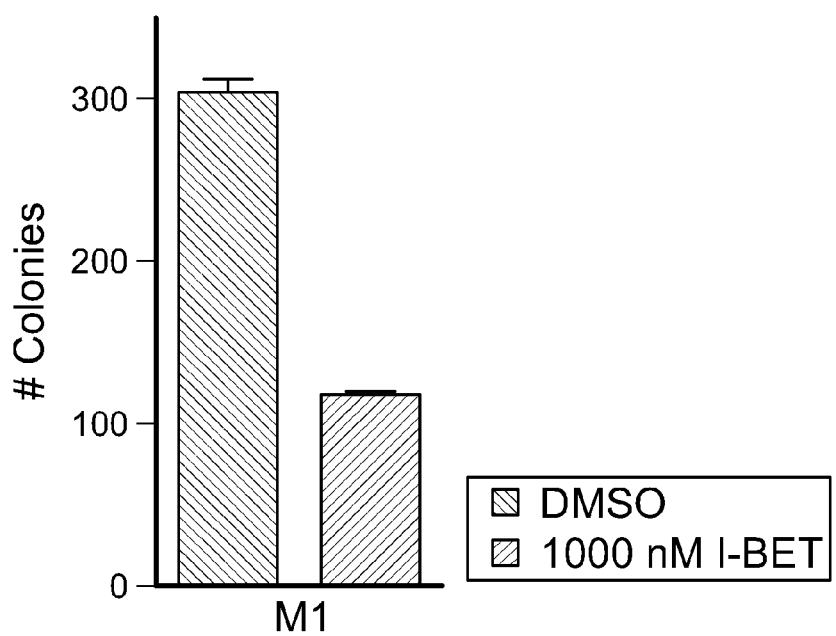

In order to understand if LSC were intrinsically resistant to I-BET, we sorted L-GMPs from mice that were I-BET naïve and challenged them with 1 µM of I-BET in clonogenic assays. Whilst this dose virtually eradicates the clonogenic potential of I-BET naïve bulk leukaemia cells (FIG. 1D), between 30-40% of L-GMPs are able to survive (FIG. 2H). Moreover, initial treatment with I-BET in vivo does not result in an immediate increase in L-GMPs; instead this population progressively emerges with continuous and sustained exposure to drug in vivo (FIG. 2F). These findings suggest that immunophenotypically homogenous L-GMP/LSC cells show marked heterogeneity in their response to I-BET and not all L-GMPs are intrinsically resistant to BET inhibitors.

Figure 3A:
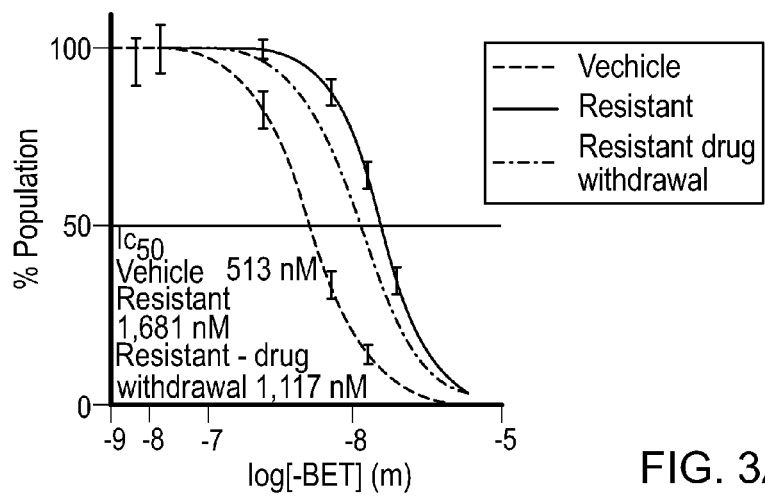
FIG. 3A-3I shows the genetic, epigenetic and transcriptional characteristics of BET-inhibitor resistant cells. (A) A graphical representation of I-BET concentration (log [I-BET] M; x-axis) against proliferation (%; y-axis) showing that BET inhibitor resistance is only partially reversible in the absence of continuing selective pressure with I-BET. (B) A graphical representation of I-BET concentration (nM; x-axis) against cell population (%; y-axis) showing that I-BET-mediated induction of cell cycle arrest is only partially restored in the absence of continuing selective pressure with I-BET. (C) A graphical representation of CD11b positive cells ($\times10^n$) against the number of Gr1 positive cells ($\times10^n$) showing that the phenotype of sensitive I-BET-naïve cells is only partially restored in the absence of continuing selecting pressure with I-BET. (D) A graphical representation of chromosome (x-axis) against copy number ratio (y-axis) showing that I-BET resistant cell lines do not demonstrate significant genomic instability when compared to parental control cell lines. (E) A graphical representation of distance (bp; x-axis) against peak count (y-axis) showing a decrease in chromatin-bound BRD4 across annotated transcriptional start sites (TSSs). (F) A graphical representation of BRD4 binding and histone 3 Lys 27 acetylation (H3K27ac) at MYC enhancer elements showing that the key BRD4 target gene, MYC, was equally expressed in resistant cells despite the loss of BRD4 from functional MYC enhancer elements. (G) A graphical representation of a principal components (PC) analysis of PC1 (x-axis) against PC2 (y-axis) showing that several transcriptional changes clearly distinguish sensitive from resistant cells. (H) A graphical representation of a gene set enrichment analysis (GSEA) of fold change (FC; x-axis) against enrichment (y-axis) showing that the GSEA of resistant cells strongly overlapped with previously published transcriptome data of LSCs from this AML model (Krivtsov et al. 2007, *Nature*, 442: 818-822; Krivtsov et al. 2013, *Leukemia*, 27:852-860). (I) A graphical representation of gene expression of WNT/β-catenin, TGF-β, PI3K/AKT/mTOR, Hippo, JAK/STAT, RAS/ERK/MAPK, NOTCH, Hedgehog and NF-κβ pathways showing that in resistant clones the WNT/β-catenin and TGF-β pathways are significantly up-regulated (P=0.036, P=0.036, respectfully; n=11), while the NF-κβ pathway is significantly down-regulated (P=0.042; n=11).
Figure 3B:
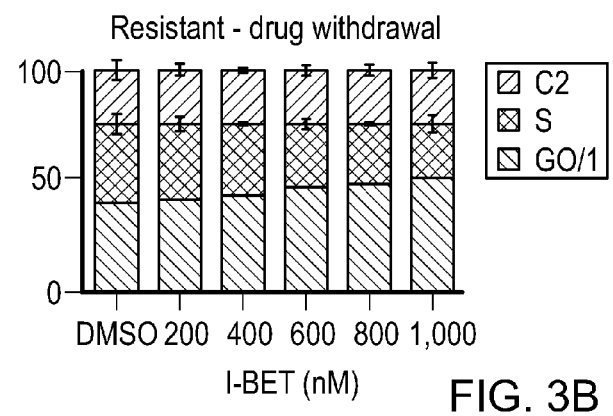
Figure 3C:
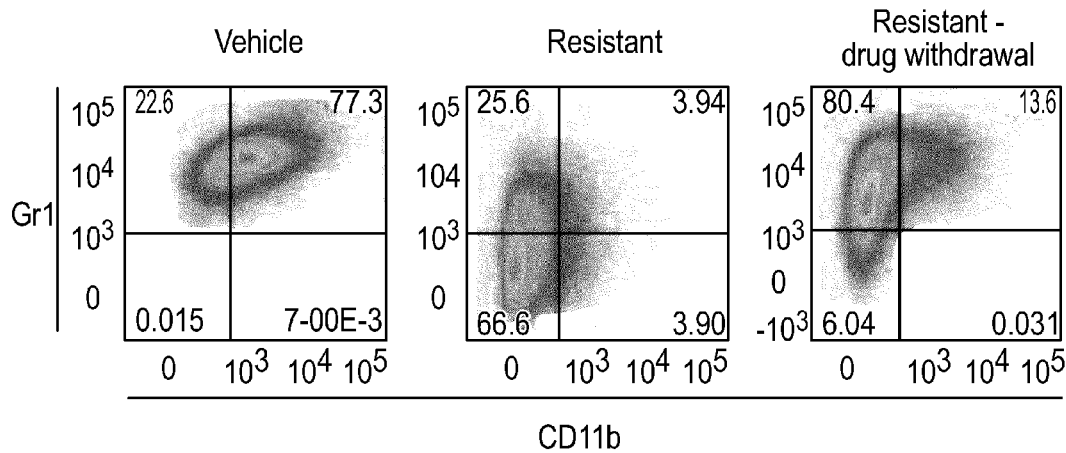

BET inhibitor sensitivity was only partially restored in the absence of ongoing selective pressure with I-BET (FIGS. 3A and B) and these cells only partially reacquire the immunophenotype of sensitive I-BET naïve cells (FIG. 3C). Moreover, transcriptionally they also adopt an intermediate state between sensitive cells and those resistant to I-BET above the $IC_{60}$ of the drug (FIG. 3G).

Figure 3D:
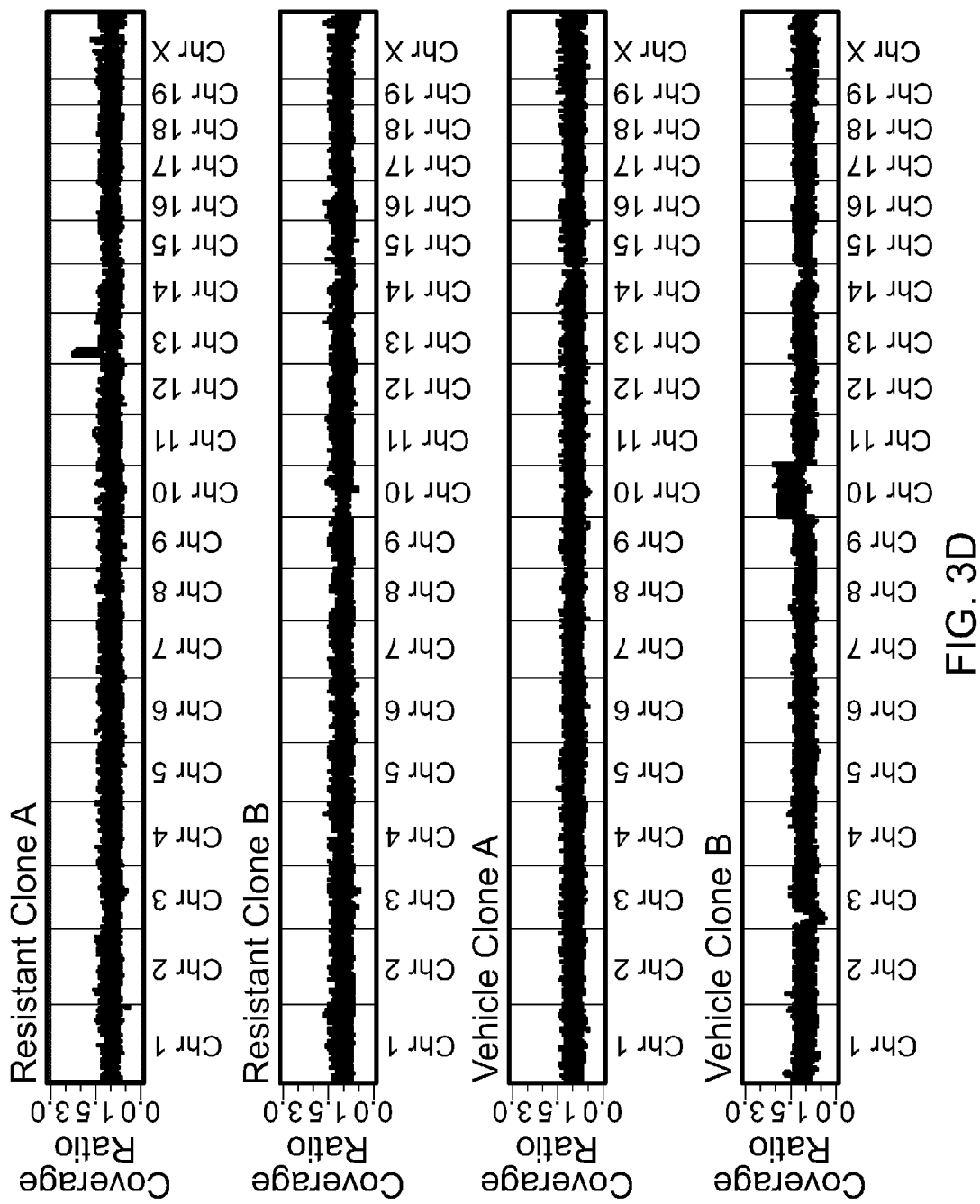

Whole exome sequencing (WES) in the parental and 2 separate vehicle/I-BET resistant cell lines was performed to further explore the molecular aetiology for BET inhibitor resistance (FIG. 3D). Importantly, although independently established resistant clones behaved identically in all functional analyses described above, there were no gatekeeper mutations in the bromodomains of BRD2/3/4 and no shared copy number aberrations. Moreover, only a few mutations with no apparent functional relevance to AML and/or BET activity were shared across several resistant cell lines (FIG. 3D).

Figure 3E:
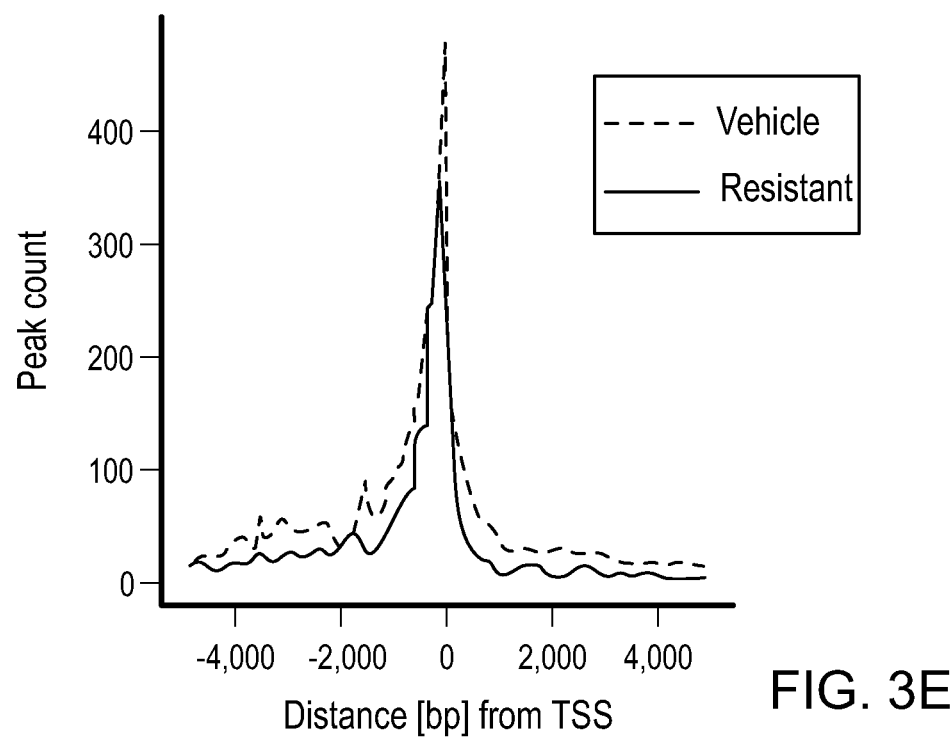
Figure 3F:
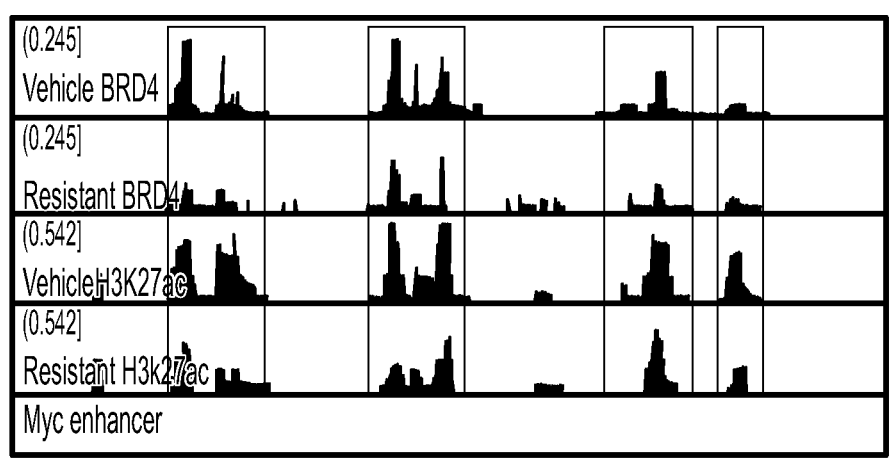

Resistant cells stably growing in I-BET showed a decrease in chromatin bound BRD2, BRD3 and BRD4 (FIG. 3E). Interestingly, however, we found that key BRD4 target genes such as MYC were equally expressed in resistant cells despite loss of BRD4 from functional MYC enhancer elements (FIG. 3F). These findings raised the prospect that alternate compensatory transcriptional programmes were active in BET resistant cells.

Figure 3G:
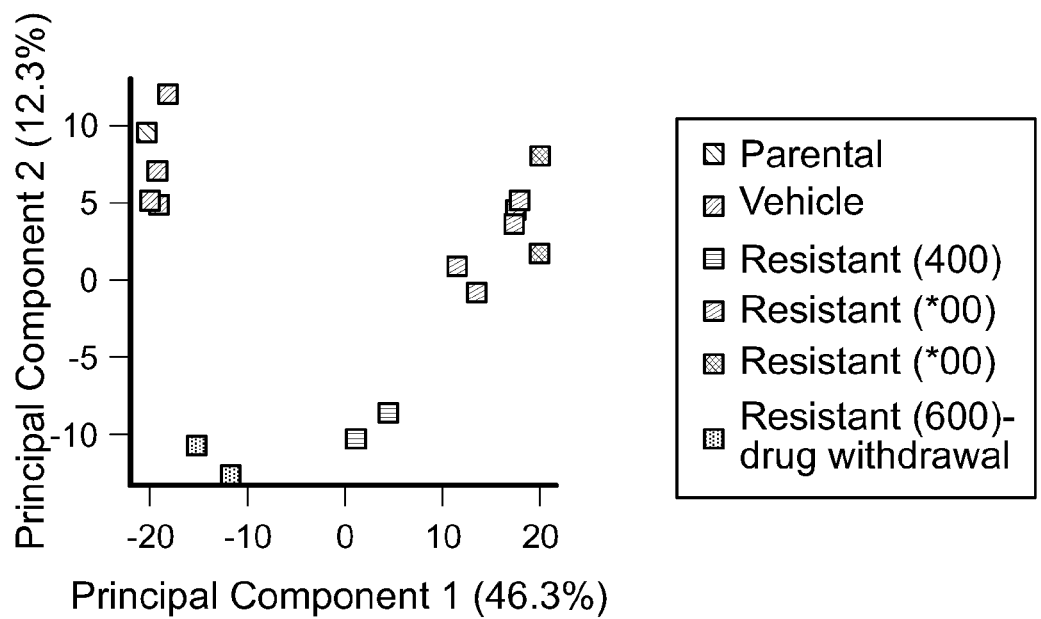
Figure 3H:
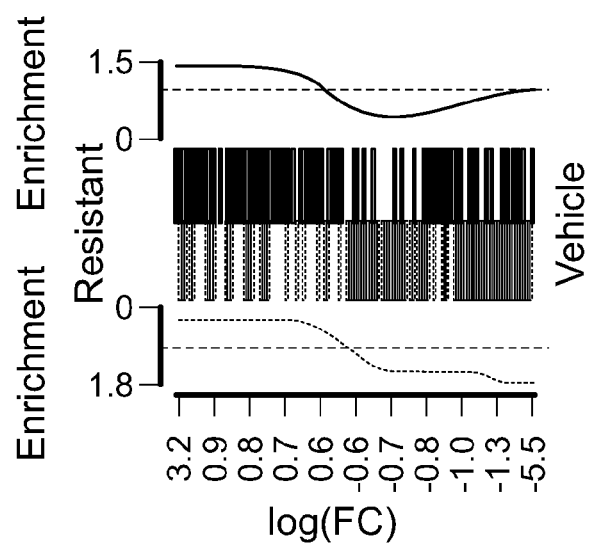
Figure 3I:
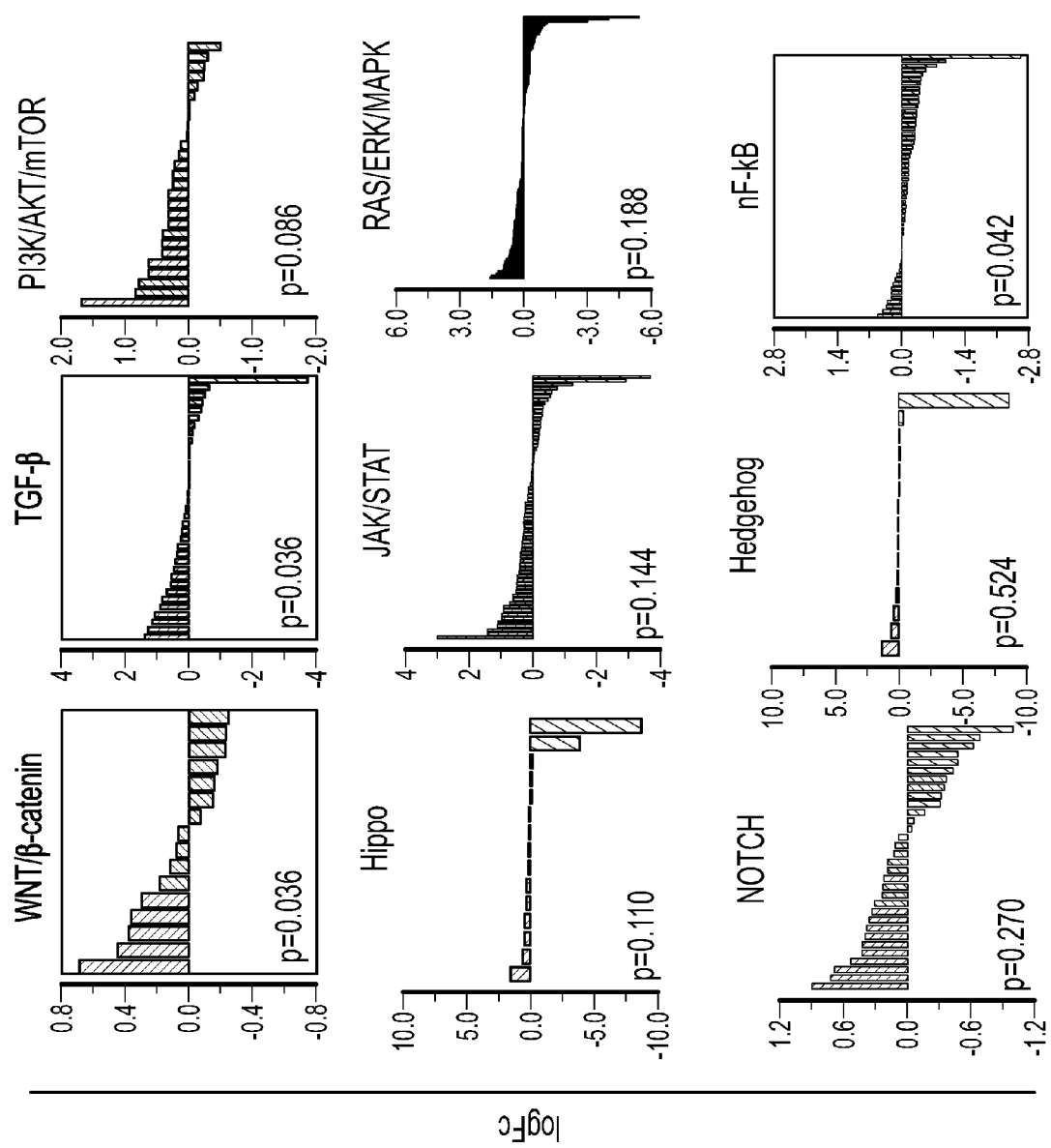
Figure 4A:
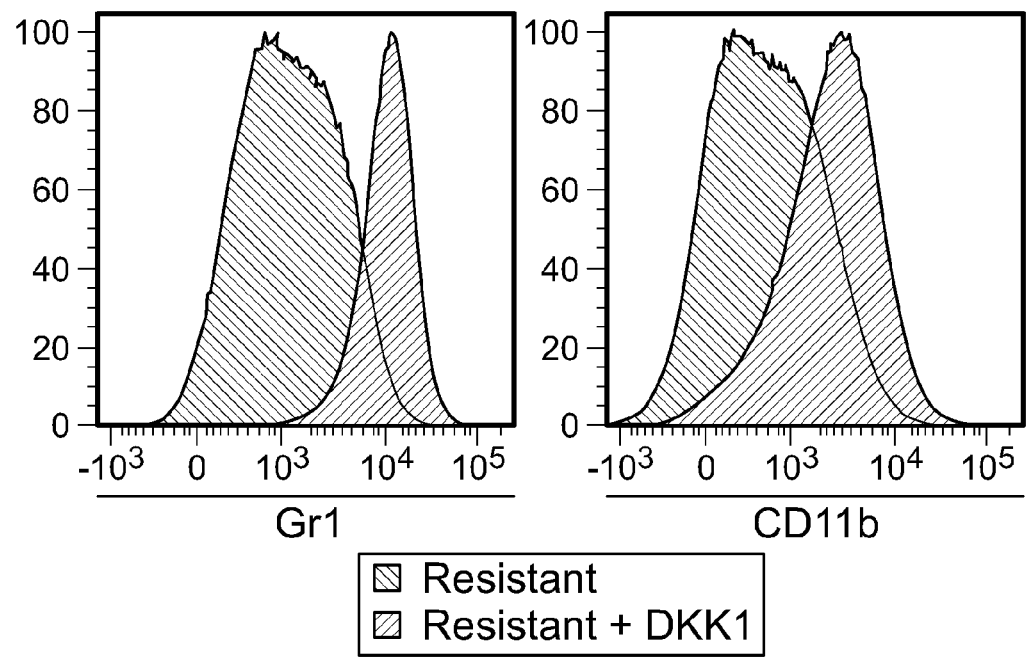
FIG. 4A-4J shows that WNT/β-catenin signalling regulates sensitivity to BET inhibition. (A) A graphical representation of Gr1 or CD11b expression (x-axis) against cell number (%; y-axis) showing that heterologous expression of Dickopf Wnt signalling pathway inhibitor (Dkk1) in resistant cells results in re-expression of differentiation markers (Gr1$^+$/CD11b$^+$). (B) A graphical representation of time (days; x-axis) against survival (%; y-axis) showing that I-BET-treated mice after syngeneic transplantation of resistant cells stably transduced with Dkk1 re-instated sensitivity to I-BET in vivo. (C) A heat map representation of Bliss interaction index across five-point dose range of an inhibitor of the Wnt/β-catenin pathway (pyrvinium) and I-BET showing that treatment with pyrvinium phenocopies the heterologous expression of Dkk1. (D) A graphical representation of time (days; x-axis) against survival (%; y-axis) showing that treatment with I-BET with pyrvinium after syngeneic transplantation of resistant cells re-instated sensitivity to I-BET in vivo. (E) A graphical representation of time (days; x-axis) against relative shRNA-positive cells (y-axis) showing that downregulation of the adenomatous polyposis coli (APC) gene by shRNA confers rapid I-BET resistance. (F) A graphical representation of MYC TSS and MYC enhancer elements (x-axis) against input (%; y-axis) in chromatin immunoprecipitation (ChIP) analysis showing that heterologous expression of Dkk1 results in the reduction of chromatin-bound β-catenin to a similar level to that of BET-I naïve cells. (G) A graphical representation of relative MYC expression showing that heterologous expression of Dkk1 in resistant cells results in reduced expression of MYC relative to the vehicle treated control cells. (H) A heat map representation of Brd4 and β-catenin chromatin occupancy ranked according to the amount of Brd4 binding in vehicle-treated control cells showing that in resistant cells chromatin occupancy of β-catenin increases where Brd4 is displaced, and this increased β-catenin occupancy is abrogated by the expression of Dkk1. (I) A graphical representation of a principal components analysis of PC1 (x-axis) against the number of apoptotic cells (fold change relative to DMSO control; y-axis) showing that the aggregate relative expression of β-catenin pathway genes correlates with responsiveness to I-BET therapy. (J) A schematic representation of the mechanism of resistance to BET inhibitor therapy in AML.
Figure 4B:
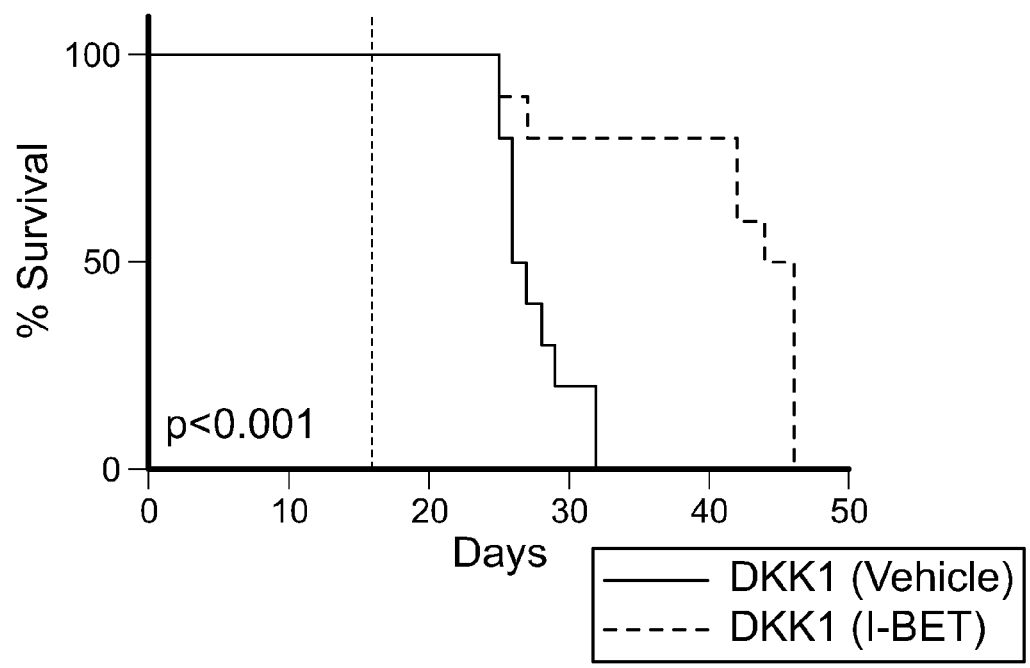
Figure 4C:
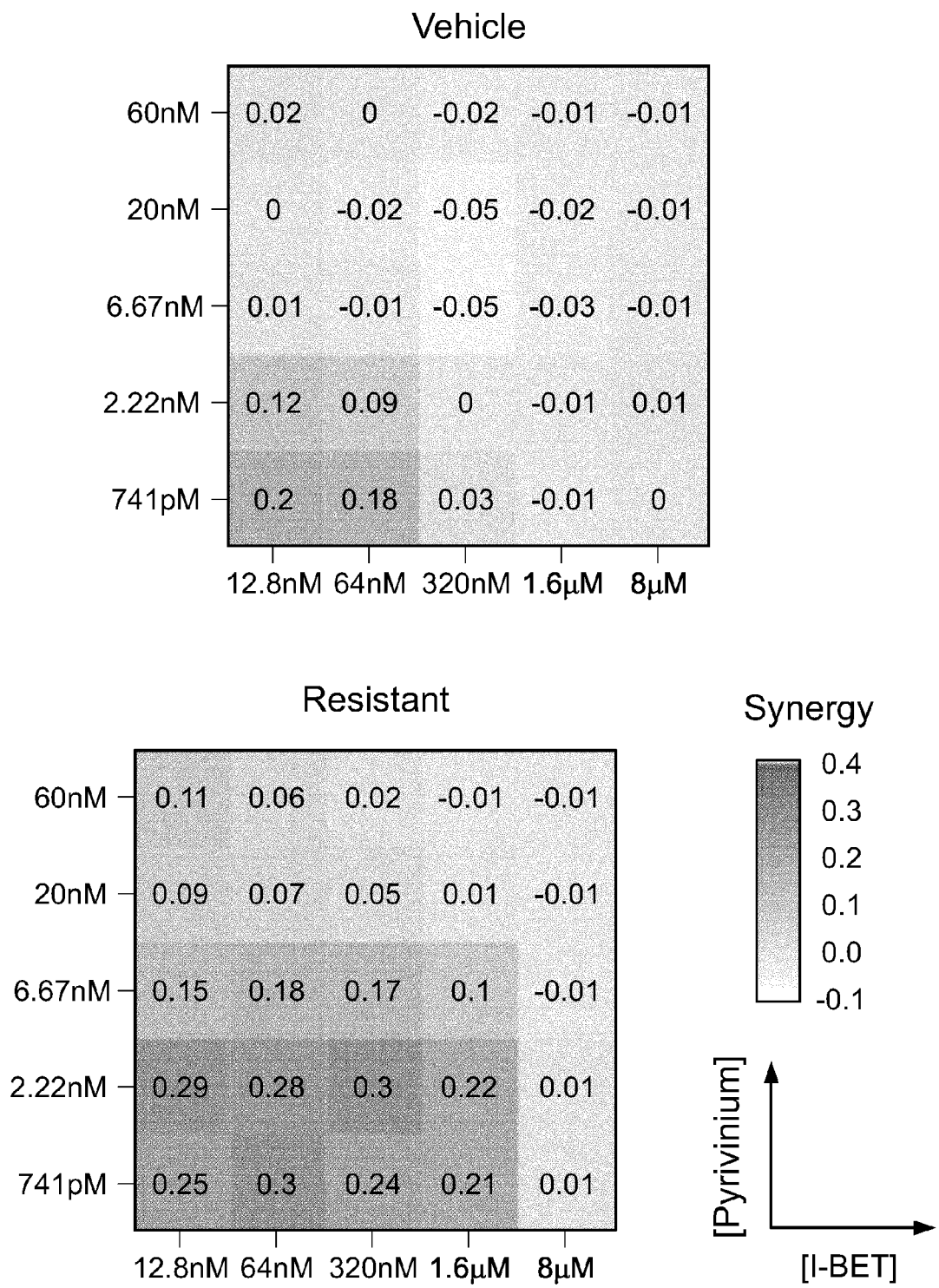
Figure 4E:
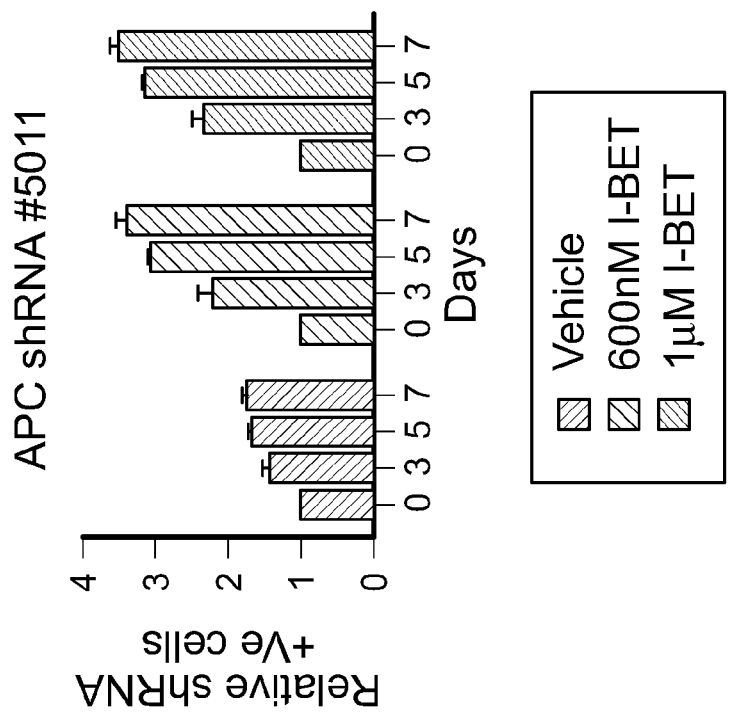
Figure 4D:
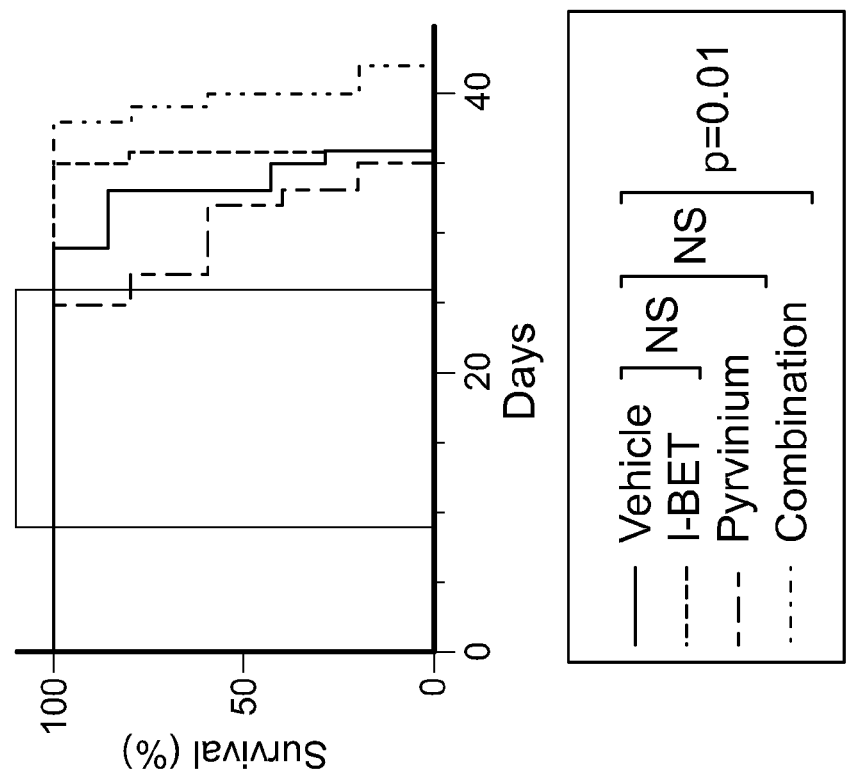
Figure 4F:
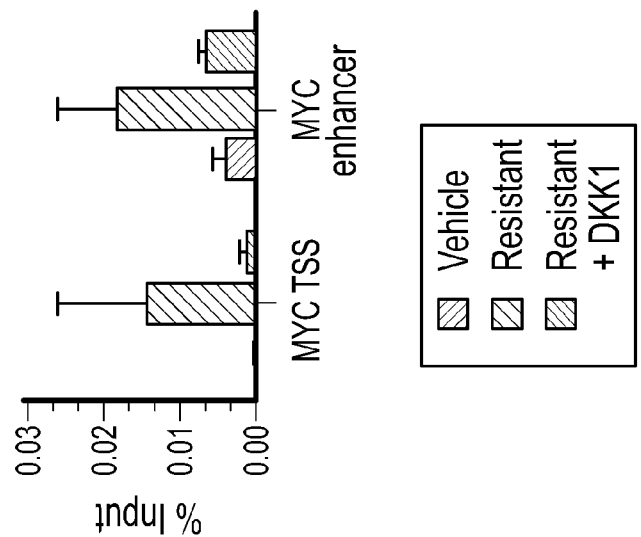
Figure 4G:
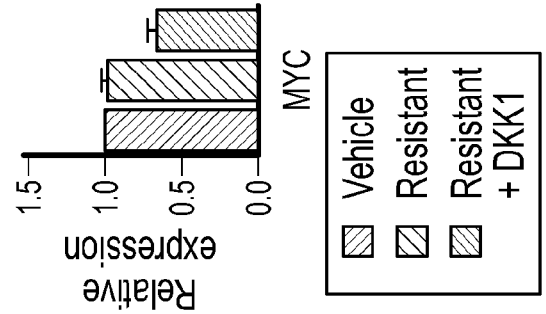
Figure 4H:
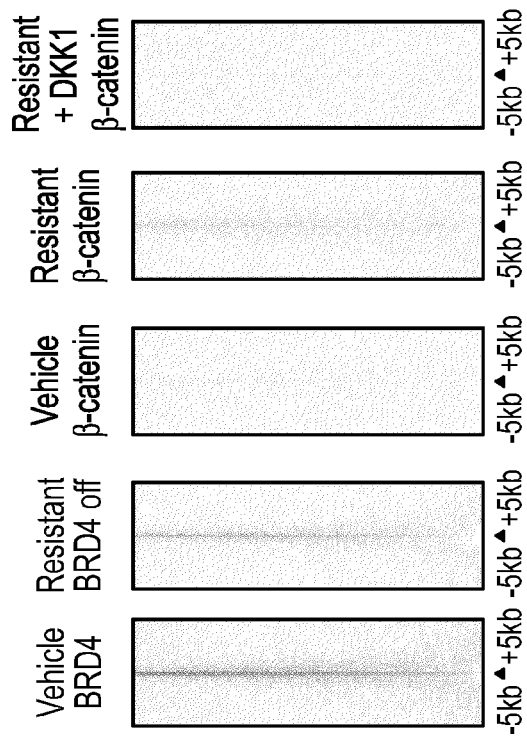
Figure 4I:
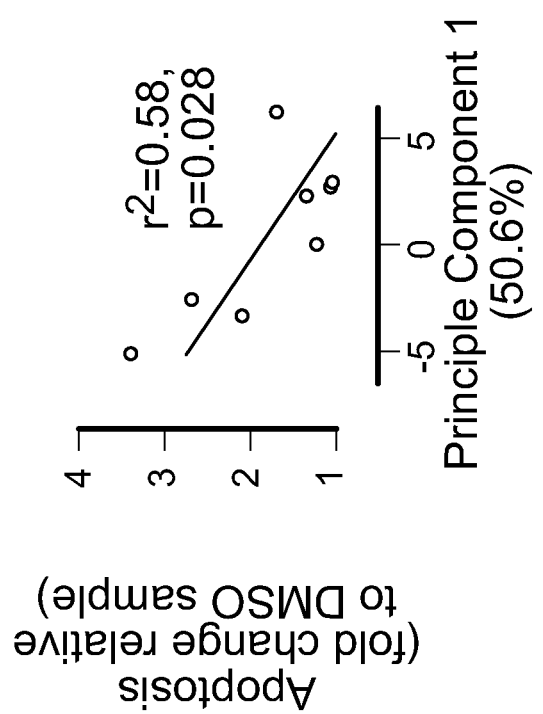
Figure 4J:
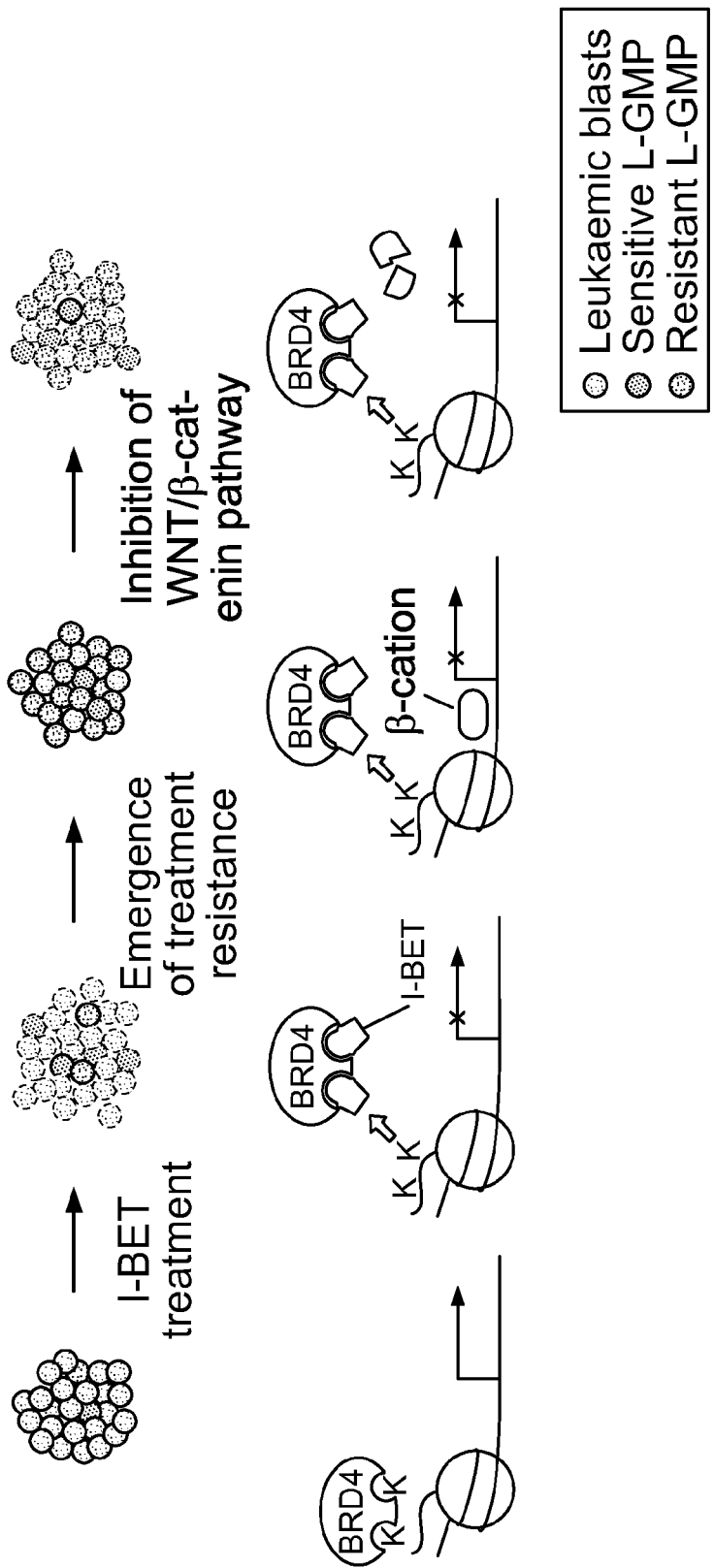

Global transcriptome analyses using 2 distinct methodologies showed a very high degree of correlation and highlighted several transcriptional changes that clearly distinguished sensitive from resistant cells (FIG. 3G). Importantly and consistent with our functional data, gene set enrichment analyses (GSEA) of our resistant cells strongly overlapped with previously published transcriptome data of LSCs from this AML model (Krivtsov et al. 2006, *Nature*, 442: 818-822; Krivtsov et al. 2013, *Leukemia*, 27: 852-860; FIG. 3H). To identify precise transcriptional programmes differentially expressed, we performed GSEA for major signalling pathways. These findings demonstrated that the NF-kB pathway was significantly down-regulated, whereas both the TGF-β and Wnt/β-catenin pathways were significantly up-regulated in our resistant cells (FIG. 3I).

REFERENCES

Benjamini and Hochberg, 1995, *Journal of the Royal Statistical Society Series B*, 57: 289-300
Cibulskis et al. 2013, *Nature Biotechnology*, 31: 213-219
Dawson et al. 2012, *New England Journal of Medicine* 367: 647-657
Dawson et al. 2011, *Nature*, 478: 529-533
Dawson et al. 2014, *Leukemia*, 28: 311-320
Eaves, 2015, *Blood*, 125(17): 2605-2613
Eppert et al. 2011 *Nature Medicine* 17: 1086-1093
Goardon et al. 2011, *Cancer Cell*, 19: 138-152
Herait et al 2014 *Cancer Research* 74: CT231
Koboldt et al. 2012, *Genome Research*, 22: 568-576
Krivtsov et al. 2006 *Nature* 442: 818-822
Krivtsov et al. 2007, *Nature*, 442: 818-822
Krivtsov et al. 2013 *Leukemia* 27: 852-860
Li and Durbin, 2009, *Bioinformatics*, 25: 1754-1760
McKenna et al. 2010, *Genome Research*, 20: 1297-1303
McLaren et al. 2010, *Bioinformatics*, 26: 2069-2070
Rathert et al. 2015, *Nature* 525: 543-547
Ritchie et al. 2015 *Nucleic Acids Research* 43(7): e47
Sahai et al. 2014, *Molecular Cancer Therapeutics* 13(7): 1907-1917
Shi and Vakoc, 2014, *Molecular Cell* 54: 728-736
Smyth in *Bioinformatics and Computational Biology Solutions using R and* Bioconductor, ed. Carey et al. 2005
Subramanian et al. 2005, *PNAS*, 102: 15545-15550
Tsirigos et al. 2012, *Bioinformatics*, 28: 282-283
Wang et al. 2010, *Science*, 327: 1650-1653
Wu et al. 2010, *Bioinformatics*, 26: 2176-2182
Zhang et al. 2008, *Genome Biology*, 9: R137
Zuber et al. 2011, *Nature*, 478: 524-528

The invention claimed is:

1. A method for preparing a mammalian leukaemia stem cell line, the method comprising:
   a. Isolating c-kit positive cells from whole bone marrow of a mammal;
   b. Immortalising the isolated cells of step (a);
   c. Serially re-plating the immortalised cells of step (b) in cytokine-supplemented methylcellulose containing a BET inhibitor;
   d. Selecting individual BET inhibitor resistant colonies and transferring to liquid culture, wherein the liquid culture contains a BET inhibitor; and
   e. Incrementally increasing the concentration of BET inhibitor in the liquid culture to greater than the IC75 value of the parental cell line, wherein the surviving cells are selected as isolated leukaemia stem cells.

2. The method according to claim 1, wherein the BET inhibitor is selected from the group consisting of I-BET 151, I-BET 762, JQ1, OTX-015, TEN-010, CPI-203, CPI-203, CPI-0610, RVX-208, PFI-1 and LY294002.

3. The method according to claim 2, wherein the BET inhibitor is selected from the group consisting of I-BET 151 and JQ1.

4. The method according to claim 3, wherein the BET inhibitor is I-BET 151.

5. The method of claim 1, wherein the c-kit positive cells of step (a) are isolated using magnetic beads or flow cytometry.

6. The method of claim 1, wherein the mammal is a mouse.

7. The method of claim 6, wherein the mouse is a C57BL/6 mouse.

8. The method of claim 1, wherein the cytokine-supplemented methylcellulose of step (c) contains a BET inhibitor at the $IC_{40}$ value of the cells.

9. The method of claim 1, wherein the concentration of BET inhibitor of step (e) is greater than the $IC_{80}$ value of the parental cell line.

10. The method of claim 1, wherein the concentration of BET inhibitor of step (e) is greater than the $IC_{90}$ value of the parental cell line.

* * * * *